US012708282B2

(12) United States Patent
Weinstein et al.

(10) Patent No.: US 12,708,282 B2
(45) **Date of Patent: *Aug. 18, 2026**

(54) LONG-TERM, CONTINUAL, WIRELESS, INTRAORAL MONITOR

(71) Applicant: UCHU Biosensors, Inc., Cambridge, MA (US)

(72) Inventors: Daniel Weinstein, Lincoln, MA (US); Saam Bozorg, West Hartford, CT (US); Noah William Hill, Tacoma, WA (US); John R. Zebryk, Jr., Southbridge, MA (US)

(73) Assignee: UCHU Biosensors, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,879

(22) Filed: Mar. 17, 2023

(65) Prior Publication Data

US 2024/0057886 A1 Feb. 22, 2024

Related U.S. Application Data

(62) Division of application No. 16/254,501, filed on Jan. 22, 2019, now Pat. No. 11,638,535.

(Continued)

(51) Int. Cl.

*A61B 5/0534* (2021.01)
*A61B 5/00* (2006.01)

(Continued)

(52) U.S. Cl.

CPC ............ *A61B 5/0534* (2013.01); *A61B 5/002* (2013.01); *A61B 5/0022* (2013.01);

(Continued)

(58) Field of Classification Search

CPC ..... A61B 5/0534; A61B 5/002; A61B 5/0022; A61B 5/14507; A61B 5/14539;

(Continued)

(56) References Cited

U.S. PATENT DOCUMENTS 4,319,578 A 3/1982 Enger
4,629,424 A 12/1986 Lauks et al.

(Continued)

FOREIGN PATENT DOCUMENTS

CA 2239397 A1 12/1998
CN 202311935 U 7/2012

(Continued)

OTHER PUBLICATIONS

Arakawa et al., "Mouthguard biosensor with telemetry system for monitoring of saliva glucose: A novel cavitas sensor," Biosensors and Bioelectronics, 84:106-111 (2016).

(Continued)

*Primary Examiner* — Andrey Shostak

(74) *Attorney, Agent, or Firm* — Foley Hoag LLP; Dana M. Gordon; Stephen J. Kenny

(57) ABSTRACT

This disclosure relates to wireless electronics designed for use within the oral cavity to measure biological or chemical variables, including pH or analyte concentrations, and transmit the measurements. More particularly, the disclosure relates to a wearable intraoral sensor comprising sensing electronics arranged within a flexible circuit mounted onto a molar band, a wireless transmission unit coupled to the sensing electronics and configured to wirelessly transmit electrical data signals to a receiver outside of the oral cavity, and a power source operably coupled to the sensing electronics and wireless transmission unit. The wearable intraoral sensor can be installed around a tooth and continu- (Continued)

ally measure and wirelessly transmit measurement data for extended periods of time without user action.

12 Claims, 9 Drawing Sheets

Related U.S. Application Data

(60) Provisional application No. 62/619,427, filed on Jan. 19, 2018.

(51) Int. Cl.
*A61B 5/145* (2006.01)
*A61B 5/1468* (2006.01)
*A61B 5/1473* (2006.01)
*G01N 27/414* (2006.01)
*G16H 40/63* (2018.01)
*A61B 5/01* (2006.01)

(52) U.S. Cl.
CPC ...... *A61B 5/14507* (2013.01); *A61B 5/14539* (2013.01); *A61B 5/1468* (2013.01); *A61B 5/1473* (2013.01); *A61B 5/4277* (2013.01); *A61B 5/682* (2013.01); *A61B 5/6831* (2013.01); *A61B 5/6882* (2013.01); *A61B 5/7282* (2013.01); *A61B 5/742* (2013.01); *A61B 5/746* (2013.01); *G01N 27/414* (2013.01); *G16H 40/63* (2018.01); *A61B 5/01* (2013.01); *A61B 5/4848* (2013.01); *A61B 5/6839* (2013.01)

(58) Field of Classification Search
CPC ... A61B 5/1468; A61B 5/1473; A61B 5/4277; A61B 5/682; A61B 5/6831; A61B 5/6882; A61B 5/7282; A61B 5/742; A61B 5/746; A61B 5/01; A61B 5/4848; A61B 5/6839; G01N 27/414; G16H 40/63; G16H 40/67; G16H 50/20; G16H 50/30; Y02A 90/10
See application file for complete search history.

(56) References Cited

U.S. PATENT DOCUMENTS 6,239,705 B1 5/2001 Glen
6,607,387 B2 8/2003 Mault
11,638,535 B2 5/2023 Weinsein et al.
12,310,752 B2 5/2025 Weinstein et al.
2004/0158194 A1 8/2004 Wolff et al.
2007/0083094 A1* 4/2007 Colburn ................ A61B 5/682 600/323
2007/0106138 A1* 5/2007 Beiski .................... A61B 5/682 600/549
2007/0282226 A1 12/2007 Longley
2008/0182218 A1 7/2008 Chen et al.
2011/0172826 A1* 7/2011 Amodei ................... C12N 1/36 700/266
2011/0184663 A1 7/2011 Mack et al.
2012/0148971 A1 6/2012 Yamamoto et al.
2013/0109932 A1 5/2013 Saadat et al.
2014/0210640 A1* 7/2014 Rahman .................. G06F 1/163 340/870.16
2015/0127377 A1 5/2015 Hashemian
2015/0170504 A1* 6/2015 Jooste .................. A61B 5/6802 340/539.12
2016/0015321 A1 1/2016 Hashemian
2016/0338626 A1 11/2016 Wang et al.
2016/0367188 A1 12/2016 Malik et al.
2017/0056131 A1 3/2017 Alauddin et al.
2017/0347953 A1 12/2017 Suri et al.
2018/0000563 A1 1/2018 Shanjani et al.
2018/0368961 A1 12/2018 Shanjani et al.
2019/0223751 A1 7/2019 Weinstein et al.
2020/0093436 A1 3/2020 Lee
2023/0030704 A1 2/2023 Weinstein et al.
2023/0082672 A1 3/2023 Weinstein et al.

FOREIGN PATENT DOCUMENTS

EP 3097411 A1 11/2016
JP 2007/064796 A 3/2007
WO WO-2005/115225 A2 12/2005
WO WO-2011/117357 A2 9/2011
WO WO-2015/112638 A1 7/2015
WO WO-2017/218947 A1 12/2017
WO WO-2021/155285 A1 8/2021

OTHER PUBLICATIONS

Brierley et al., “How Accurate are TheraMon® Microsensors at Measuring Intraoral Wear-time? Recorded vs. Actual Wear Times in Five Volunteers,” Journal of Orthodontics, 44(4):241-248 (2017).
Choi, “Continuous measurement of intra-oral pH and temperature: development, validation of an appliance and a pilot study,” 42(8):563-570 (2015).
Davidson, “In-Mouth Measurement of pH and Conductivity during Eating,” J Agric. Food Chem., 46(12): 5210-5214 (1998).
Extended European Search Report for EP Application No. 19740972.5 dated Sep. 30, 2021.
Farella et al., “Simultaneous wireless assessment of intra-oral pH and temperature,” Journal of Dentistry, 51:49-55 (2016).
Fujii et al., “Roughness and pH changes of enamel surface induced by soft drinks in vitroapplications of stylus profilometry, focus variation 3D scanning microscopy and micro pH sensor,” Dental Materials Journal, 30(3):404-410 (2011).
Gou et al., “Carbon Nanotube Chemiresistor for Wireless pH Sensing,” Scientific Reports, 4(4468):1-6 (2014).
International Search Report and Written Opinion for International Application No. PCT/US2021/015899 dated Jun. 3, 2021.
International Search Report and Written Opinion for International Application No. PCT/US19/14630 dated Jun. 25, 2019.
Kitasako et al., “The clinical application of surface pH measurements to longitudinally assess white spot enamel lesions,” Journal of Dentistry, 38(7):584-590 (2010).
Kolahi et al., “Bluetooth technology for prevention of dental caries,” Medical Hypotheses, 73:1067-1068 (2009).
Ma et al., “A wireless system for continuous in-mouth pH monitoring,” 2017 IEEE Biomedical Circuits and Systems Conference (BioCAS), Oct. 19-21, 2017.
Machacek, ““Tasting device monitors sodium intake in hypertension patients,”” retrieved Mar. 13, 2019 from https://phys.org/news/2016-01-device-sodium-intake-hypertension-patients.html (2016).
Mahendran, “Bluetoolh for While Tooth,” Journal of Operative Dentistry and Endodontics, 2(2):61-64 (2017).
Mannoor et al., “Graphene-based wireless bacteria detection on tooth enamel,” Nature Communications, 3(763):1-9 (2012).
Mayanagi et al., “pH Response and Tooth Surface Solubility at the Tooth/Bacteria Interface,” Caries Research, 51(2):160-166 (2017).
Moritsuka et al., “Quantitative assessment for stimulated saliva flow rate and buffering capacity in relation to different ages,” Journal of Dentistry, 34(9):716-720 (2006).
National Institutes of Health, Fact Sheet—Salivary Diagnostics, National Institutes of Health Updated Oct. 2010, pp. 1-2.
Potyrailo et al., Battery-free radio frequency identification (RFID) sensors for food quality and safety, J Agric Food Chem., 60(35):8535-8543 (2012).
Potyrailo et al., “Passive multivariable RFID pH sensors,” 2011 IEEE International Conference on RFID-Technologies and Applications, Sep. 15-16, 2011.
Tsuruzoe et al., “Development of the pH measurement sensor to be mounted on the oral measurement device,” 2016 International Symposium on Micro-NanoMechatronics and Human Science (MHS), Nov. 28-30, 2016.

(56) References Cited

OTHER PUBLICATIONS

Yamada et al., "A Microftuidic pH Measurement Device with a Flowing Liquid Junction," Sensors, 17(7):1563 (2017).
Extended European Search Report for EP Application No. 25177270.3 dated Sep. 2, 2025.

* cited by examiner

FIG. 1
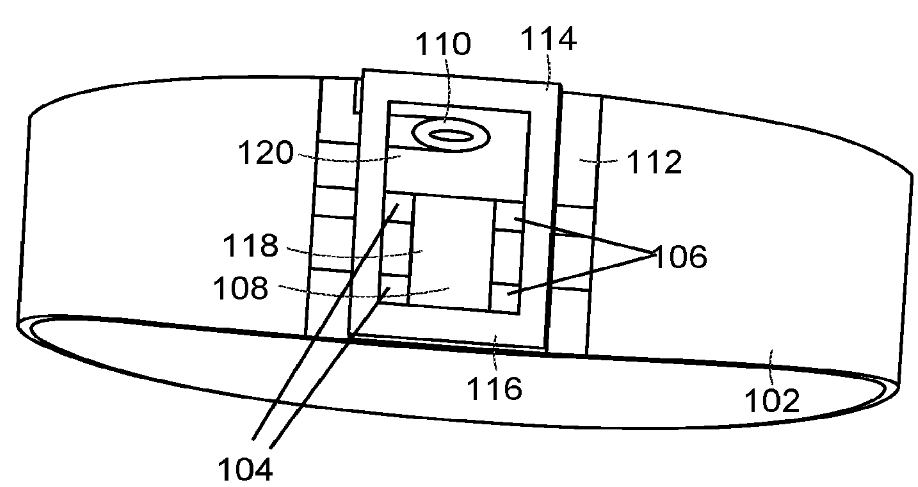
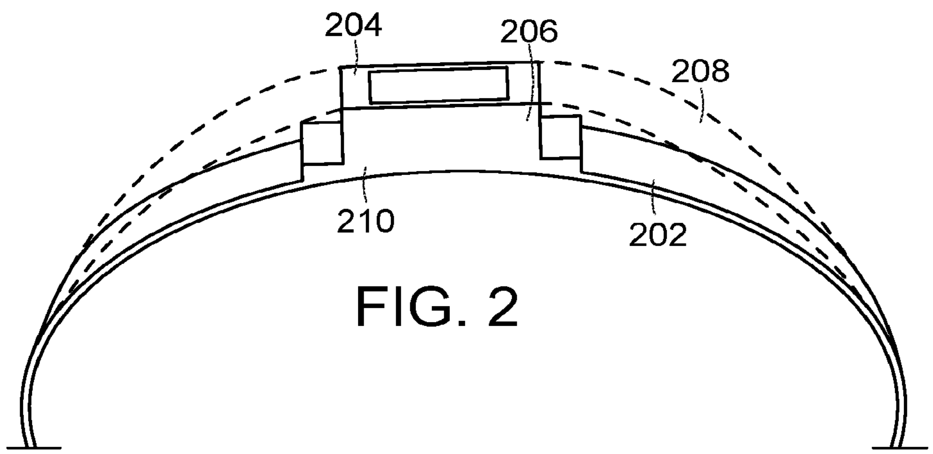
FIG. 2

Figure 14:
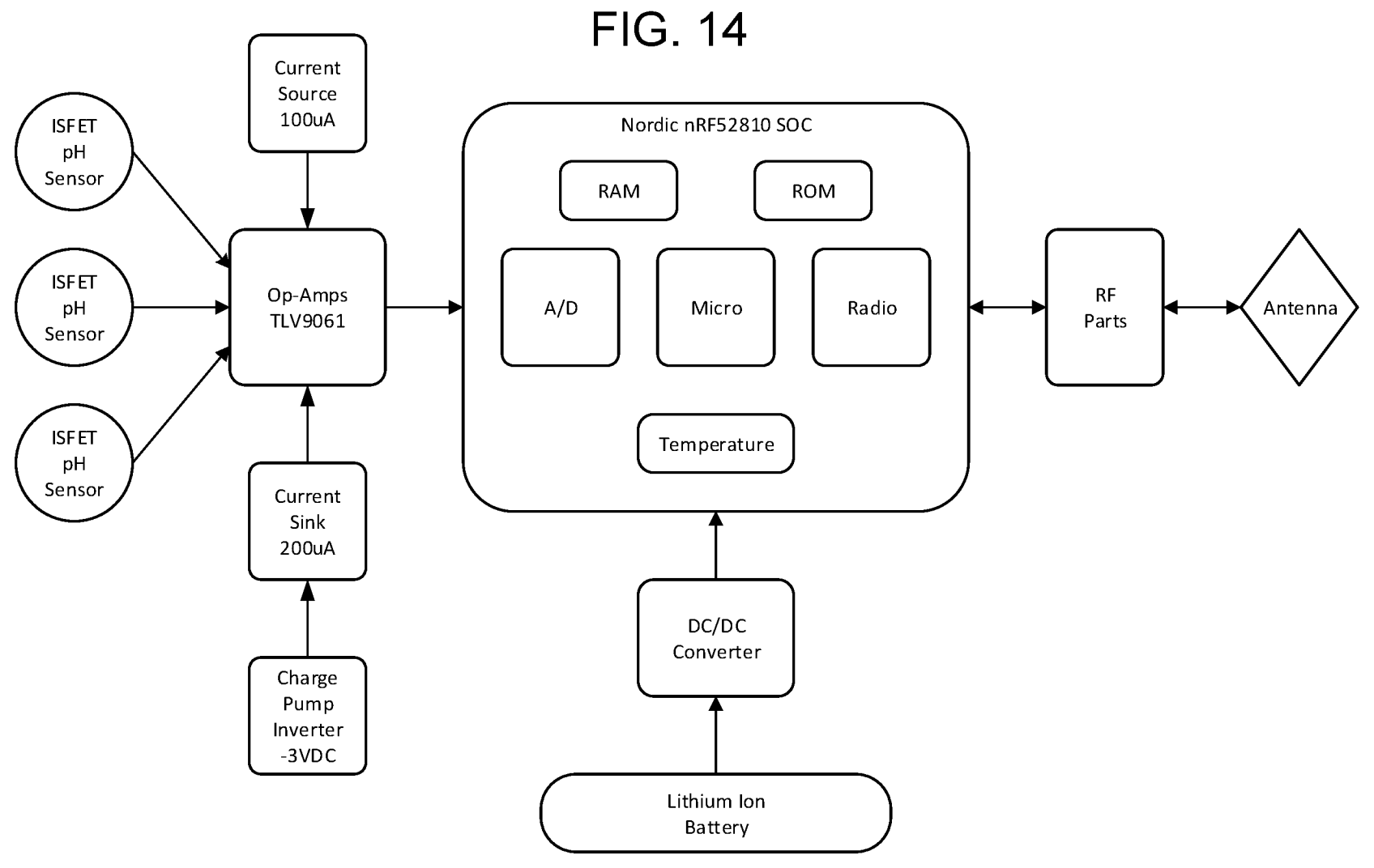

Antenna

RF Parts

Nordic nRF52810 SOC

RAM

ROM

A/D

Micro

Radio

Temperature

DC/DC Converter

Lithium Ion Battery

Current Source 100uA

Op-Amps TLV9061

Current Sink 200uA

Charge Pump Inverter -3VDC

ISFET pH Sensor

ISFET pH Sensor

ISFET pH Sensor

LONG-TERM, CONTINUAL, WIRELESS, INTRAORAL MONITOR

PRIORITY

This application is a Continuation of U.S. Non-Provisional application Ser. No. 16/254,501, filed on Jan. 22, 2019, which claims priority to U.S. Provisional Application No. 62/619,427, filed Jan. 19, 2018. The entire contents of each of these applications are incorporated herein by reference.

FIELD

This disclosure relates to wireless electronics designed for use within the oral cavity to continually measure biological or chemical variables, including pH or temperature or analyte concentrations, and wirelessly transmit the measurements.

BACKGROUND

Caries disease (cavities) is a widespread health problem in the United States. According to the CDC, 60% of American children ages 2 through 18 have this disease, making it the most common chronic disease in kids. 92% of adults ages 19 through 64 experience caries at some point in their lives and 25% of adults over 65 years of age do not have any teeth left, due to untreated decay. Low salivary pH is directly related to caries disease. Caries is caused by the action of acids on the surface of teeth, which slowly demineralize the enamel once the plaque pH drops below 5.5. The acid is produced when sugars from food and drink interact with bacteria present in the dental biofilm (plaque) on the surface of teeth. A healthy patient's salivary pH ranges between 6.2 and 7.6 with occasional drops following eating or drinking. Once the pH drops below 5.5 (the critical pH of enamel) the oral environment is under-saturated with mineral ions relative to tooth's mineral content and enamel begins to dissolve and lose calcium and phosphate in a process known as demineralization. Saliva plays an important role in buffering plaque acids and halting demineralization by providing a reservoir of minerals from which the enamel can re-mineralize and "heal". The demineralization and remineralization of enamel occurs many times throughout the day. Caries progresses only when demineralization exceeds remineralization. The typical treatment option for caries is to drill out the decay and put in a filling (restoration). Patients with extensive caries need a crown, root canal treatment, or extraction of the tooth. If left untreated, infections can develop and spread systemically to vital organs such as the eye, causing blindness, and to the brain or heart where they can be lethal.

Research suggests the need for a major shift in the way tooth decay is managed by dentists. There is a movement towards a more preventive approach compared to the formerly practiced paradigm of just "drilling and filling." Preventative, evidence-based Caries Risk Assessment (CRA) protocols have become the standard of care for prevention and official policy in dental education. The goals of such protocols are to stop or reverse caries by catching them at the earliest stages, i.e., before damage becomes irreversible and restorative intervention is necessary. Caries risk assessment is the current standard for providing preventative care. The existing standardized caries risk assessment methods, like those established by the American Dental Association (ADA), American Academy of Pediatric Dentistry (AAPD), and Caries Management by Risk Assessment (CAMBRA), are time-consuming, and rely on subjective surveys and questionnaires, thus rendering them inaccurate and underused outside of dental school clinics. All risk factors assessed by protocols such as CAMBRA are meant to help the dentist determine when and for how long a patient's oral pH is critically low which provides insight into when and for how long demineralization is out-weighing remineralization; the basis of determining a patient's caries risk level. However, there is no objective tool capable of measuring a patient's risk. There is currently no effective method of monitoring saliva characteristics or pH over time to provide a sufficient understanding of a patient's risk.

Salivary pH testing is part of CAMBRA protocol. Currently, dentists use a one time, color changing, paper pH strip. The dentist dips the pH strip into a sample of resting saliva and may infer the pH of the saliva using the color of the strip and a color calibration guide. However, the single use, high user input level, and analog reading methods of the pH strips make them underused in dental settings. Furthermore, a one-time reading of salivary pH does not convey sufficient information regarding the conditions of the oral cavity, the potential development of caries disease, or the development of caries disease.

All of the recent approaches to measure concentration of oral analytes or pH present many problems that limit their effectiveness, usability, and commercialization. Blood tests are invasive, can cause pain, and require samples to be sent to a laboratory. Salivary samples are a snapshot in time and must be sent to a laboratory. Some intraoral devices require wires exiting the mouth for data transmission, some are uncomfortable and irritate tissue in the patient's mouth, some interfere with a patient's occlusion, some disrupt a patient's daily routine, some require significant patient compliance, some are only applicable for short term pH measurement, some require new application methods unfamiliar to dentists, and some must be uniquely fabricated for a patient's mouth. Methods and devices for long term, continual, salivary monitoring that are comfortable, inexpensive, safe, and do not affect a patient's daily routine are needed to help patients and dentists identify the cause and severity of caries progression.

SUMMARY

One aspect of this disclosure provides a system for continually monitoring pH in an oral cavity of a subject. The system comprises a wearable intraoral sensor installed on a molar in the oral cavity of the subject. The wearable intraoral sensor comprises: a molar band sized to fit around the molar of the subject. The wearable intraoral sensor also comprises a sensor unit coupled to the molar band and comprising: a transducer configured to continually measure pH in the oral cavity for at least one day, to generate pH measurement data, and to transduce the pH measurement data to a signal suitable for transmission; a data transmission unit operably connected to the transducer and configured to wirelessly transmit the signal comprising pH measurement data; and a power source operably coupled to the transducer and the data transmission unit. The wearable intraoral sensor also comprises a housing unit sealably coupled to the molar band, thereby enclosing the sensor unit inside the housing unit. The housing unit also comprises a proton exchange membrane configured to conduct protons into the sensor unit. The system also comprises a receiving device external to the oral cavity of the subject and configured to receive the pH measurement data wirelessly transmitted from the wearable intraoral sensor.

In some embodiments, the transducer comprises an ISFET sensor.

In some embodiments, the molar band is configured as an antenna operably connected to the wireless transmission unit.

In some embodiments, the wearable intraoral sensor wirelessly transmits the signal comprising pH measurement data at intervals. In certain embodiments, the wearable intraoral sensor transmits the data signal once per minute. In some embodiments, the wearable intraoral sensor wirelessly transmits the data signal once every five minutes. In other embodiments, the wearable intraoral sensor wirelessly transmits the data signal once every ten minutes. In still other embodiments, the wearable intraoral sensor wirelessly transmits the data signal between once every minute and once every 30 minutes. In further embodiments, the wearable intraoral sensor wirelessly transmits the data signal immediately after the data signal is generated. In still further embodiments, the wearable intraoral sensor wirelessly transmits the data signal at a specified time. In some embodiments, the wearable intraoral sensor is configured to wirelessly transmit the data signal once per millisecond. In some embodiments, the wearable intraoral sensor is configured to wirelessly transmit the data signal when the power source has a threshold level of power.

In certain embodiments, the wearable intraoral sensor is configured to wirelessly transmit the data signal at intervals for at least one day, one week, one month, two months, three months, or six months.

In some embodiments, the wearable intraoral sensor is configured to continually measure pH in the oral cavity for at least one week, one month, two months, three months, or six months.

In further embodiments, the receiving device is a smart device. In certain embodiments, the smart device is a smart phone, a smart watch, a tablet, smart home device (e.g., an Amazon Echo™ or other device using Amazon Alexa™, a Google Home™ device, or an Apple Home Pod™ or other device using Apple's Siri™) or a computer. In still further embodiments the smart device is an iPhone or Android device. In further embodiments, the receiving device comprises a display.

In some embodiments, the system further comprises an application installed on the receiving device or smart device. In some embodiments, the application is configured to receive the pH measurement data. In certain embodiments, the application is configured to manipulate the pH measurement data. In some embodiments, the application is configured to display the pH measurement data or a manipulation thereof. In further embodiments, the application is configured to display the pH measurement data or manipulation thereof in graphical form. In still further embodiments, the application is configured to receive subject identifying information, location information, device type information, or a combination thereof. In other embodiments, the application is configured to send subject data to a third party. In certain embodiments, the subject data comprises pH measurement data, subject identifying information, location information, device type, or a combination thereof. In further embodiments, the application is configured to mask or remove subject-identifying information prior.

In further embodiments, the application is configured to display an alert comprising a message about the development of caries disease or the risk of development of caries disease. In still further embodiments, the application is configured to display an advice message comprising suggestions to treat caries disease or inhibit the development of caries disease.

In other embodiments, the system further comprises criteria for diagnosing caries disease or the risk of development of caries disease. In further embodiments, the system further comprises criteria for diagnosing a disorder or the risk of development of a disorder.

Another aspect of this disclosure is directed to a wearable intraoral sensor for continually measuring pH in an oral cavity of a subject. The wearable intraoral sensor comprises a molar band sized to fit around a molar in an oral cavity of a subject. The wearable intraoral sensor also comprises a sensor unit or module coupled to the molar band. The sensor unit or module comprises a transducer configured to measure pH in an oral cavity and transduce the pH measurement to a data signal suitable for transmission. The sensor unit or module also comprises a data transmission unit operably connected to the transducer and configured to wirelessly transmit the data signal. The sensor unit or module also comprises a power source operably connected to the transducer and the data transmission unit. The wearable intraoral sensor also comprises a housing unit sealably coupled to the molar band, thereby sealing the sensor unit inside the housing unit. The wearable intraoral sensor also comprises a proton exchange membrane configured to conduct protons into the sensor unit. In some embodiments, the housing unit comprises the proton exchange membrane. In some embodiments, the sensor unit or module comprises the proton exchange membrane. The wearable intraoral sensor is configured to continually measure pH in the oral cavity and to wirelessly transmit the data signal at intervals for a least one day.

In some embodiments, the molar band is configured as an antenna operably connected to the wireless transmission unit.

In some embodiments, the molar band does not interfere with occlusion, speaking, or swallowing in the oral cavity.

In some embodiments, the transducer comprises an ISFET sensor.

In some embodiments, the wearable intraoral sensor further comprises memory configured to store pH measurement data.

In some embodiments, the wearable intraoral sensor wirelessly transmits the data signal at intermittent intervals. In certain embodiments, the wearable intraoral sensor wirelessly transmits the data signal once per minute. In some embodiments, the wearable intraoral sensor wirelessly transmits the data signal once every five minutes. In other embodiments, the wearable intraoral sensor wirelessly transmits the data signal once every ten minutes. In still other embodiments, the wearable intraoral sensor wirelessly transmits the data signal between once every minute and once every 30 minutes. In further embodiments, the wearable intraoral sensor wirelessly transmits the data signal immediately after the data signal is generated. In still further embodiments, the wearable intraoral sensor wirelessly transmits the data signal at a specified time. In some embodiments, the wearable intraoral sensor is configured to wirelessly transmit the data signal once per millisecond. In some embodiments, the wearable intraoral sensor is configured to wirelessly transmit the data signal when the power source has a threshold level of power.

In certain embodiments, the wearable intraoral sensor is configured to wirelessly transmit the data signal at intervals for at least one day, one week, one month, two months, three months, or six months.

In some embodiments, the wearable intraoral sensor is configured to continually measure pH in the oral cavity for at least one week, one month, two months, three months, or six months.

In some embodiments, the wearable intraoral sensor wirelessly transmits via Bluetooth technology. In other embodiments, the wearable intraoral sensor wirelessly transmits via a wireless local area network (WLAN), Wi-Fi (wireless fidelity), ZigBee, near-field communication (NFC), ANT, Thread, Zigbee, WiMAX, WWAN, MANET, PAN, Wireless Hart, Z-Wave, MESH, UWB, IrDA, Cellular, Peer-To-Peer, and 802.11 variants. In still other embodiments, the wearable intraoral sensor wirelessly transmits via frequencies ranging from sub-sonic to ultraviolet. In further embodiments, the wearable oral sensor wirelessly transmits using modulation methods including, but not limited to, OOK, AM, FM, SSB, FSK, PSK, GFSK, and MSK. In still further embodiments, the wearable oral sensor wirelessly transmits using Near Field, Mid Field, or Far Field magnetic and or electric field radiation.

In some embodiments, the data signal further comprises instructions executable by a processor in a mobile device to send the data to an application installed on the mobile device.

Another aspect of this disclosure is directed to a method for continually measuring pH in an oral cavity of a subject. The method comprises installing a wearable intraoral sensor around a molar in a subject's oral cavity. The wearable intraoral sensor comprises a molar band sized to fit around the molar; a sensor module coupled to the molar band and comprising a transducer, a data unit, a power source operably coupled to the data unit, and a proton exchange membrane. The wearable intraoral sensor also comprises a housing unit containing a portion of the sensor module and coupled to the molar band. The wearable intraoral sensor is configured to continually measure pH in the oral cavity for at least one day. The method also comprises continually measuring pH in the subject's oral cavity for at least one day, thereby generating pH measurement data. The method also comprises wirelessly transmitting the pH measurement data from the molar band at intervals.

In some embodiments, the molar band is configured as an antenna operably connected to the wireless transmission unit.

In some embodiments of the method, the transducer comprises an ISFET sensor.

In some embodiments, the method further comprises orienting the proton exchange membrane or sensor unit buccally in the oral cavity of the subject.

In some embodiments, the method further comprises wirelessly transmitting the data signal at intervals for at least one day, one week, one month, two months, three months, or six months. In some embodiments, the method comprises continually measuring pH in the oral cavity of the subject for at least one week, one month, two months, three months, or six months.

In certain embodiments, the data signal is wirelessly transmitted once per minute. In some embodiments, the data signal is wirelessly transmitted once every five minutes. In other embodiments, the data signal is wirelessly transmitted once every ten minutes. In still other embodiments, the data signal is wirelessly transmitted between once every minute and once every 30 minutes. In further embodiments, the data signal is wirelessly transmitted immediately after the data signal is generated.

In some embodiments, the method further comprises wirelessly transmitting the pH measurement data from the molar band at intervals to a receiving device. In some embodiments, the receiving device is a smart device. In certain embodiments, the smart device is a smart phone, a smart watch, a tablet, smart home device (e.g., an Amazon Echo™ or other device using Amazon Alexa™, a Google Home™ device, or an Apple Home Pod™ or other device using Apple's Siri™) or a computer. In still further embodiments the smart device is an iPhone or Android device.

In some embodiments, the method further comprises configuring the receiving device to receive the pH measurement data from the molar band. In certain embodiments, configuring a receiving device to receive the pH measurement data from the molar band comprises installing an application on the receiving device or smart device.

In some embodiments, the method further comprises transmitting subject data from the receiving device or smart device to a third party. In certain embodiments, the method further comprises transmitting subject data to a doctor, dentist, medical office, dental office, parent of the subject, relative, insurance agency, or an insurance office. In other embodiments, the method further comprises transmitting subject data from the receiving device or smart device to a research office. In still other embodiments, the method further comprises comprising syncing data from the wearable intraoral sensor and the receiving device.

In further embodiments, subject data comprises pH measurement data, subject identifying information, location information, or device type (i.e., the type of receiving device).

Another aspect of this disclosure is directed to a method of installing a wearable intraoral sensor of this disclosure in an oral cavity of a subject. The wearable intraoral sensor comprises a molar band; a sensor module coupled to the molar band and comprising a transducer, a wireless transmission unit, a power supply operably connected to the wireless transmission unit and the transducer, and a proton exchange membrane; and a housing unit containing the sensor module and coupled to the molar band and enclosing the sensor unit. The method comprises selecting a molar in the oral cavity of the subject. Next, the method comprises selecting or sizing the wearable intraoral sensor to fit around the selected molar. The method also comprises creating space around the molar, applying adhesive to the molar band of the wearable intraoral sensor, and installing the wearable intraoral sensor around the molar. The method also comprises wirelessly syncing or connecting the wearable intraoral sensor to a receiving device.

In further embodiments, the receiving device is a smart device. In certain embodiments, the smart device is a smart phone, a smart watch, a tablet, smart home device (e.g., an Amazon Echo™ or other device using Amazon Alexa™, a Google Home™ device, or an Apple Home Pod™ or other device using Apple's Siri™) or a computer. In still further embodiments the smart device is an iPhone or Android device. In further embodiments, the receiving device comprises a display.

In some embodiments, the transducer comprises an ISFET sensor.

In some embodiments, the method further comprises orienting the sensor unit or proton exchange membrane buccally in the oral cavity of the subject.

In further embodiments, the method further comprises syncing or connecting the wearable intraoral sensor to an application installed on the mobile device. In still further embodiments, the method further comprises adding identifying information of the subject to the application.

A further aspect of this disclosure is directed to a method of diagnosing caries disease or the risk of developing caries disease in a subject. In some embodiments, the method comprises installing a wearable intraoral sensor of this disclosure around a molar in the subject's oral cavity and syncing or connecting the wearable intraoral sensor with a receiving device. In some embodiments, the method comprises syncing or connecting a wearable intraoral sensor installed around a molar in the oral cavity of a subject with a receiving device. The method also comprises measuring pH in the subject's oral cavity for at least one day, thereby generating pH measurement data. The method also comprises receiving the pH measurement data in an application on the receiving device. The method comprises comparing the pH measurement data to criteria for caries disease, wherein caries disease is diagnosed, or the risk of caries disease is diagnosed, when the pH measurement data meets the criteria.

In some embodiments, the molar band is configured as an antenna operably coupled to the wireless transmission unit.

In some embodiments, the transducer comprises an ISFET sensor.

In some embodiments, the method further comprises orienting the sensor unit or proton exchange membrane buccally in the oral cavity of the subject.

In some embodiments, the method also comprises wirelessly transmitting the pH measurement data to a receiving device. In certain embodiments, the pH measurement data is transmitted wirelessly at intervals. In some embodiments, the interval is one minute. In certain embodiments, the interval is 5 minutes. In some embodiments, the interval is five minutes. In other embodiments, the interval is ten minutes. In still other embodiments, the interval is from 1 to 30 minutes. In yet other embodiments, the method comprises wirelessly transmitting pH measurement data immediately after the data signal is generated. In still further embodiments, the method comprises wirelessly transmitting the data signal at a specified time. In some embodiments, the method comprises wirelessly transmitting the data signal once per millisecond. In some embodiments, the method comprises wirelessly transmitting the data signal when the power source has a threshold level of power.

In certain embodiments, the method comprises wirelessly transmitting the data signal at intervals for at least one day, one week, one month, two months, three months, or six months.

In some embodiments, the method comprises continually measuring pH in the oral cavity for at least one week, one month, two months, three months, or six months.

In some embodiments, the pH measurement data is transmitted wirelessly via Bluetooth technology.

In some embodiments, the pH in the subject's oral cavity is measured for at least one week. In certain embodiments, the pH in the subject's oral cavity is measured for at least one month.

In further embodiments, the method further comprises identifying a time period that pH in the oral cavity was below a set value on a plurality of days. In some embodiments, the set value is pH 5.5.

In further embodiments, the receiving device is a smart device. In certain embodiments, the smart device is a smart phone, a smart watch, a tablet, smart home device (e.g., an Amazon Echo™ or other device using Amazon Alexa™, a Google Home™ device, or an Apple Home Pod™ or other device using Apple's Siri™) or a computer. In still further embodiments the smart device is an iPhone or Android device. In further embodiments, the receiving device comprises a display.

In other embodiments, the method further comprises displaying the pH measurement data or a manipulation thereof on a display of the mobile device. In particular embodiments, the pH measurement data or manipulation thereof is displayed in graphical form.

In still further embodiments, the method further comprises sending the pH measurement data to a third party. In some embodiments, the third party is a doctor, dentist, medical office, dental office, parent of the subject, relative, insurance agency, an insurance office, or a research office. In still other embodiments, the method further comprises adding the pH measurement data to a medical record of the subject. In yet further embodiments, the method further comprises sending the pH measurement data to a research institution. In yet other embodiments, the method further comprises sending the pH measurement data to a corporation. In still other embodiments, the method further comprises removing or masking subject identifying information.

Another aspect of this disclosure is directed to an automated method of warning a subject about the potential development of caries disease. In some embodiments, the method comprises installing a wearable intraoral sensor of this disclosure around a molar in a subject's oral cavity. In some embodiments, the method comprises syncing or connecting an installed wearable intraoral sensor with a receiving device. The method comprises measuring pH in the subject's oral cavity for at least one day, thereby generating pH measurement data. The method also comprises receiving the pH measurement data in an application on the receiving device; comparing the pH measurement data to criteria for caries disease, and displaying a message on a display of the smart device when the criteria is met, thereby warning the subject about the potential development of caries disease.

In some embodiments, the transducer comprises an ISFET sensor.

In some embodiments, the molar band is configured as an antenna operably connected to the wireless transmission unit.

In some embodiments, the method further comprises orienting a sensor unit or proton exchange membrane of the wearable intraoral sensor buccally in the oral cavity of the sensor.

In some embodiments, the method comprises wirelessly transmitting the pH measurement data to the receiving device. In further embodiments, the pH measurement data is transmitted wirelessly at intervals. In some embodiments, the interval is one minute. In certain embodiments, the interval is 5 minutes. In some embodiments, the interval is five minutes. In other embodiments, the interval is ten minutes. In still other embodiments, the interval is from 1 to 30 minutes. In yet other embodiments, the pH measurement data is wirelessly transmitted immediately after the data signal is generated. In some embodiments, the method comprises wirelessly transmitting the data signal once per millisecond. In some embodiments, the method comprises wirelessly transmitting the data signal when the power source has a threshold level of power.

In some embodiments, the method further comprises wirelessly transmitting the data signal at intervals for at least one day, one week, one month, two months, three months, or six months. In some embodiments, the method comprises continually measuring pH in the oral cavity of the subject for at least one week, one month, two months, three months, or six months.

In some embodiments, the pH measurement data is transmitted wirelessly via Bluetooth technology.

In some embodiments, pH in the subject's oral cavity is measured for at least one week. In certain embodiments, pH in the subject's oral cavity is measured for at least one month. In further embodiments, the method further comprises identifying a time of day that pH in the oral cavity was below a set value on a plurality of days. In some embodiments, the set value is pH 5.5. In some embodiments, the method further comprises drawing inferences from the identified time periods related to the lifestyle, or health or habits of the subject.

In some embodiments, the method further comprises displaying the pH measurement data or a manipulation thereof on a display of the mobile device. In certain embodiments, the pH measurement data or manipulation thereof is displayed in graphical form.

In still further embodiments, the method further comprises sending the pH measurement data to a third party. In some embodiments, the third party is a doctor, dentist, medical office, dental office, parent of the subject, relative, insurance agency, an insurance office, or a research office. In still other embodiments, the method further comprises adding the pH measurement data to a medical record of the subject. In yet further embodiments, the method further comprises sending the pH measurement data to a research institution. In yet other embodiments, the method further comprises sending the pH measurement data to a corporation. In still other embodiments, the method further comprises removing or masking subject identifying information.

In still other embodiments, the method further comprises removing or encrypting subject identifying information. In some embodiments, removing or encrypting subject identifying information and subject data complies with applicable medical industry standards (e.g., such steps are HIPAA compliant).

In further embodiments, the message comprises information about the development of caries disease or the risk of development of caries disease. In still further embodiments, the method comprises displaying an advice message comprising suggestions to treat caries disease or inhibit the development of caries disease.

Another aspect of this disclosure is directed to a method of diagnosing a disorder or the potential for development of a disorder in a subject. The method comprises syncing or connecting a wearable intraoral sensor of this disclosure, installed around a molar in the subject's oral cavity, with a receiving device. The method comprises measuring an analyte in the subject's oral cavity for at least one day, thereby generating analyte measurement data. The method also comprises receiving the analyte measurement data in an application on the receiving device and comparing the analyte measurement data to criteria for a disorder. A disorder is diagnosed or the potential for a disorder is diagnosed when the analyte measurement data meets the criteria for a disorder.

In some embodiments, the disorder is selected from the group consisting of caries disease, periodontal disease, gastroesophageal reflux disease (GERD), heart disease, and, osteoporosis, metabolic acidosis, metabolic alkalosis, and kidney disease. Caries leads to poor oral health which has been shown to be related to cardiovascular disease and diabetes.

In some embodiments, the transducer comprises an ISFET sensor.

In some embodiments, the method further comprises orienting the sensor unit or proton exchange membrane of the wearable intraoral sensor buccally in the oral cavity of the subject.

In some embodiments, the method comprises wirelessly transmitting the analyte measurement data to a receiving device. In some embodiments, the method comprises wirelessly transmitting the analyte measurement data at intervals. In certain embodiments, the intervals are minutes. In certain embodiments, the interval is 5 minutes. In some embodiments, the interval is five minutes. In other embodiments, the interval is ten minutes. In still other embodiments, the interval is from 1 to 30 minutes. In yet other embodiments, the method comprises wirelessly transmitting analyte measurement data immediately after the data signal is generated. In some embodiments, the method comprises wirelessly transmitting the analyte measurement data once per millisecond. In some embodiments, the method comprises wirelessly transmitting the analyte measurement data when the power source has a threshold level of power. In further embodiments, the method further comprises wirelessly transmitting the analyte measurement data at intervals for at least one day, one week, one month, two months, three months, or six months.

In some embodiments, the method further comprises wirelessly transmitting the data signal at intervals for at least one day, one week, one month, two months, three months, or six months. In some embodiments, the method comprises continually measuring analyte in the oral cavity of the subject for at least one week, one month, two months, three months, or six months.

In some embodiments, the analyte measurement data is transmitted wirelessly via Bluetooth technology.

In some embodiments, the analyte is measured for at least one week. In further embodiments, the analyte is measured for at least one month.

In some embodiments, the method further comprises displaying the analyte measurement data or a manipulation thereof on a display of the mobile device. In certain embodiments, the analyte measurement data or manipulation thereof is displayed in graphical form. In further embodiments, the method comprises sending the analyte measurement data to a third party. In some embodiments, the third party is selected from the group consisting of a doctor, dentist, medical office, dental office, parent of the subject, relative, insurance agency, an insurance office and a research office.

In some embodiments, the method further comprises displaying an advice message on the display, wherein the advice message comprises suggested corrective action to treat the disorder or inhibit the development of the disorder.

The present disclosure provides an Ion Selective Field Effect Transistor (ISFET) based pH sensor that may be comfortably inserted into the user's mouth, worn for extended periods of time (e.g., months), is biocompatible with the oral environment, has the capability to wirelessly transmit pH measurements, is unaffected from most other dynamic oral variables, and resists biofilm growth. In some embodiments, the sensor's components are attached to a molar band and include an encased ISFET transducer and power and transmission electronics including an RF chip, voltage divider circuit, and analog to digital converter. In some embodiments, the described sensor is worn on one tooth and is easily installed and removed. The sensor of this disclosure overcomes many long felt but unsolved challenges including pH specificity, accuracy, size, sensing lifetime, biocompatibility, comfort, effort-free data collection, patient non-compliance, and power requirements.

BRIEF DESCRIPTION OF THE FIGURES

FIG. 1 depicts sensor housing mounted on metal molar band

FIG. 2. depicts a perspective view of sensor housing mounted on a molar band.

FIG. 3. is a perspective view of a wearable intraoral sensor.

FIG. 14 depicts an exemplary block diagram for an embodiment of a wearable intraoral sensor.

DETAILED DESCRIPTION

Figure 4:
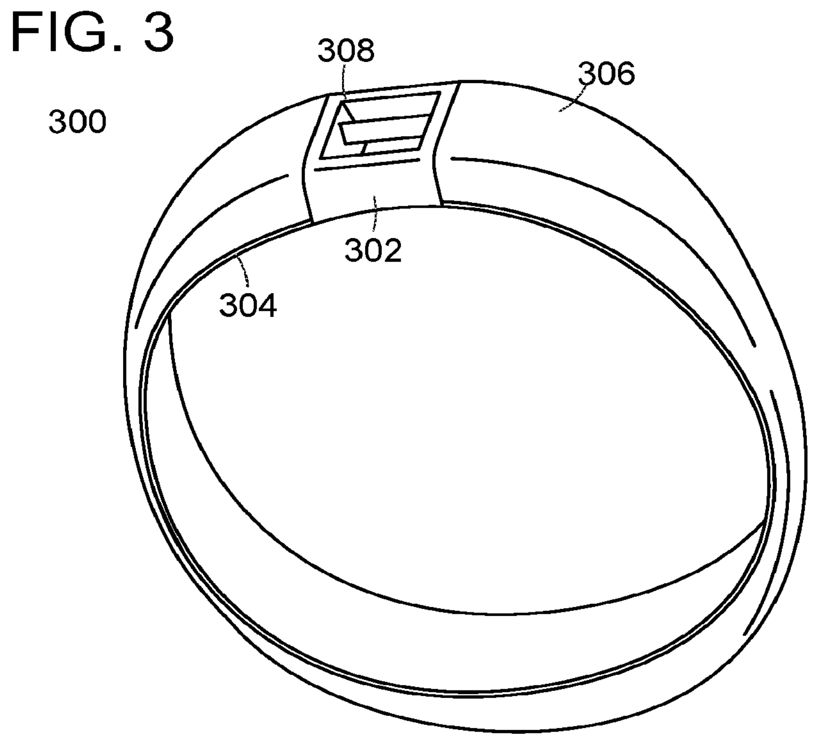
FIG. 4 is a perspective view of a wearable intraoral sensor with enclosed electronics for power, transmission, and transducing.

This disclosure provides wearable intraoral sensors for non-invasive continual measurement and long-term use in a subject's oral cavity and wireless transmission of measurement data. In some embodiments, the disclosure provides a biosensor transducer fit for measuring pH values for extended periods of time (e.g., months) in complex oral environments. In some embodiments, the sensor can measure analytes or other variables in an oral environment. The main design considerations for this sensor include the sensor's specificity and accuracy, size, sensing lifetime, biocompatibility, comfort, and power requirements. In some embodiments, the wearable intraoral sensor transduces and transmits pH values, while accounting for other changing variables such as salivary flow rate, tissue contact, temperature, salivary turbidity, salivary viscosity, ionic strengths, and jaw movements. The accuracy of the pH measurements is comparable to the accuracy of conventional pH sensors like glass membrane sensors. In some embodiments, the transducer and other components should be small enough to fit on the side of a tooth. In some embodiments, the sensor is able to maintain its accuracy for a period of months and does not experience significant fouling due to mineral or food deposition or bacterial growth. The sensor is comfortable for the user to wear long term, which involves optimizing the sensor-gum interface, sensor-cheek interface, and ensuring the sensor does not occlude or alter the user's bite. In some embodiments, the operational power requirements of the wearable intraoral sensor are small enough to be feasibly powered by a mechanism that can also fit onto a tooth. Finally, the wearable intraoral sensors do not require subject action, thereby eliminating or reducing the potential for subject non-compliance.

As used herein, the term "about" means+/−10% of a stated value. As used herein, the term "subject" means a human or an animal. In some embodiments, a subject is a mammal. Exemplary animals include mouse, rat, rabbit, guinea pig, dog, cat, horse, cow, pig, monkey, chimpanzee, baboon, rhesus monkey, sheep, and goat. As used herein, the terms "disorder", "disease", and "condition" are used interchangeably for a condition in a subject. As used herein, the terms "smart device" and "mobile device" are used interchangeably to mean any portable computing device comprising a processor and a display. For example, mobile device and smart devices include, but are not limited to, mobile phones, smart phones, smart watches, tablets, and laptops.

Wearable Intraoral Sensors

One aspect of this disclosure provides a wearable intraoral sensor for continually measuring pH or one or more analytes or temperature, or a combination thereof, in an oral cavity in a subject for a time period of at least one day. The wearable intraoral sensor comprises a dental installation. In some embodiments, the dental installation is a molar band sized to fit around a molar in an oral cavity of a subject. The wearable intraoral sensor also comprises a sensor unit coupled to the dental installation and comprising a transducer configured to measure pH or temperature or one or more analytes, or a combination thereof, in an oral cavity in a subject and transduce the measurement data to a data signal suitable for transmission; a data transmission unit operably connected to the transducer and configured to wirelessly transmit the data signal; and a power source operably connected to the transducer and the data transmission unit. In some embodiments, the sensor unit comprises a transducer enclosure enclosing the transducer and comprising a semi-permeable membrane configured to allow desired molecules to enter the transducer enclosure. In some embodiments, the sensor unit comprises a transducer enclosure enclosing the transducer and comprising a proton exchange membrane configured to allow protons to enter the transducer enclosure. The wearable intraoral sensor also comprises a housing unit sealably coupled to the dental installation. The housing unit is configured to seal the electronics inside the housing unit. The transducer enclosure can be part of the sensor unit or the housing unit.

In some embodiments, the housing unit comprises a transducer enclosure enclosing the transducer and comprising a semi-permeable membrane configured to allow desired molecules to enter the transducer enclosure. In some embodiments, the housing unit comprises a transducer enclosure enclosing the transducer and comprising a proton exchange membrane configured to allow protons to contact the transducer. In some embodiments, the housing unit sealably couples to the dental installation and seals the electronics inside (i.e., at least the transducer, data transmission unit, and power source). In certain embodiments, the housing unit sealably couples around a whole molar band or to a portion of a molar band.

The housing unit comprises a semi-permeable membrane configured to allow protons or desired molecules or ions to enter the sensor unit. In some embodiments, the housing unit and sensor unit are combined into one unit so that the sensor unit and housing unit are not separate. In some embodiments, the electronics of the sensor unit are integrated into the housing unit. In some embodiments, the semi-permeable membrane is a proton exchange membrane configured to conduct protons into the sensor unit. The wearable intraoral sensor is configured to continually measure or detect pH or temperature or one or more analytes, or a combination thereof, in the oral cavity and wirelessly transmit the data signal for a least one day.

In some embodiments, the dental installation is a molar band sized to fit around a molar in an oral cavity of a mammal. Molar bands have numerous advantages over other dental devices. For one, they are non-invasive. Two, most dentists have experience installing molar bands. Three, molar bands do not interfere with occlusion in a subject's oral cavity. Four, molar bands do not need to be custom-made for each subject prior to being installed.

In some embodiments, the dental installation is a dental crown (also called a "dental cap"). In other embodiments, the dental installation is a dental implant, bridge, dentures, orthodontic temporary anchorage device (TAD), a removable dental prosthesis, a removable dental appliance including, but not limited to, Herbst appliance, Activator, Bionator, twin block appliance, Pendulum appliance, Forus™ Fatigue Resistant Device, Hyrax appliance, Haas appliance, Hawley-type removable appliance with jackscrew, Quad-helix, W-arch, transpalatal arch, Nance appliance, Lower lingual arch, and an aligners (e.g., Invisalign™).

In some embodiments, the wearable intraoral sensor measures pH in an oral cavity of a subject. Periods of elevated acidity occur on the span of tens of minutes and can indicate why and when teeth are decaying. Existing devices are incapable of continually measure acidity data for extended time periods, which is critical for monitoring acid attacks and preventing caries. Existing devices (e.g., mouthguards, retainers) are too large to wear in the mouth throughout the day, require effort from the user to operate or maintain which reduces compliance and completeness of data, have short sensor lifetimes, and/or have inadequate durability to survive oral conditions.

In other embodiments, the wearable intraoral sensor measures or detects one or more analytes in an oral cavity of a subject. In some embodiments, the analyte is avian influenza virus, hepatitis B marker HBsAg, cancer marker AFP, human thyroid stimulating hormone, interleukin 8 (IL-8), tumor necrosis factor (TNF-$\alpha$), cancer biomarker CYFRA21-1, prostate cancer biomarker PSA, carcinoembryonic antigen (CEA), cardiac troponin I (cTnI), C-reactive protein (CRP), prostate cancer biomarker osteopontin (OPN), interleukin-6 (IL-6), cortisol, lyme disease antigen, Alzheimer biomarker amyloid-$\beta$, chondroitin sulfate proteoglycan 4, pancreatic cancer biomarker, carbohydrate antigen 19-9 (CA 19-9), prostate specific antigen/1-antichymotrypsin (PSA-ACT) complex, breast cancer biomarkers human epidermal growth factor receptor 2, human immunodeficiency virus (HIV), bladder cancer biomarker, urinary APOA2 protein, prostate cancer biomarker PSA-ACT complex, D-Dimer, biomarker of venous thromboembolism, breast cancer biomarker EGFR, hemoglobin-A1c, insulin. Additional analytes are described in Ana Carolina, *Recent Trends in Field-Effect Transistors-Based Immunosensors*, Chemosensors 2016, 4, 20, 21 Oct. 2016 (accessed here: http://www.mdpi.com:8080/2227-9040/4/4/20/pdf), which is herein incorporated by reference.

In further embodiments, the analyte is an analyte detectable in saliva. In certain embodiments, the analyte is a hormone such as cortisol, androgens, testosterone, estriol, estrogen, progesterone, aldosterone, DHEAS. In other embodiments, the analyte is an antibody such as IgG, IgA, sIgA, IgM. In some embodiments, the analyte is a growth factor such as EGF, NGF, VEGF, IGF. In some embodiments, the analyte is selected from cytokines and chemokines such as IL-1 beta, IL-8, IL-6, MCP-1, CX3CL1, GRO-1 alpha, troponin I, TNF alpha. In some embodiments, the analyte is selected from nucleic acids such as human DNA, microbial DNA, mRNA, siRNA, micro RNA (miR-125a and miR-200a). In still other embodiments, the analyte is a protein detectable in saliva. In other embodiments, the analyte is a drug, including, but not limited to, drugs of abuse, ethanol, therapeutic drugs, anticonvulsants, antipyretic/analgesics, anti-neoplastic agents, anti-bacterial agents, bronchodilators, and cotinine. Additional analytes that can be measured or detected are described in Malamud D, *Saliva As A Diagnostic Fluid*, Dent Clin North Am. 2011 January; 55(1):159-78 (accessed here: https://www.ncbi.nlm.nih.gov/pubmed/21094724).

In additional embodiments, the analyte is selected from analytes that are consumed during eating and drinking. These analytes include nutritional macromolecules such as carbohydrates, proteins, and fats; allergens such as shellfish, peanuts, gluten, etc.; and toxins such as heavy metals, mercury, etc.

In further embodiments, the wearable intraoral sensor measures temperature in the oral cavity of a subject. In still further embodiments, the wearable intraoral sensor measures a combination of pH, temperature, and/or one or more analytes in an oral cavity of a subject.

In some embodiments, the wearable intraoral sensor is configured to measure or detect pH, temperature, one or more analytes, or a combination thereof, in an oral cavity of a subject for at least one week. In other embodiments, the wearable intraoral sensor is configured to measure or detect pH, temperature, one or more analytes, or a combination thereof, in an oral cavity of a subject for at least one week. In further embodiments, the wearable intraoral sensor is configured to measure or detect pH, temperature, one or more analytes, or a combination thereof, in an oral cavity of a subject for a defined time period. In still further embodiments, the wearable intraoral sensor is configured to measure or detect pH, temperature, one or more analytes, or a combination thereof, in an oral cavity of a subject for a time period ranging from one day to six months.

The wearable intraoral sensors of this disclosure take a user's comfort into account. A user's comfort while using the intraoral sensor is determined by several factors. First, the intraoral sensor should not noticeably interfere with user's occlusion (bite), speaking, or swallowing. The intraoral sensor should not protrude above the bottom molar or below the top molar, as this would create a noticeable interference with the user's occlusion. Second, the intraoral sensor's surface should not cause discomfort to the surrounding tissues of the gum, cheek, or tongue. In some embodiments, the wearable intraoral sensors of this disclosure comprise a smooth outer surface free from pockets or rough or jagged spots. In some embodiments, the electronics are coated with a smooth material, which is resistant to degradation in the mouth.

In some embodiments, the wearable intraoral sensor comprises a sensor unit coupled to the dental installation, e.g., a molar band, dental crown, dental implant, bridge, dentures, orthodontic anchor, and/or any dental prosthesis.

The transducers of this disclosure are low power, produce an easily readable signal, are small, are easily and inexpensively produced, and accurately sense in in-vivo conditions.

The transducers comprise conditioning circuitry (also known as "signal processing" circuitry). Other devices use antimony, glass electrodes, iridium/iridium oxide and imaging sensors, which are either too large or fragile or produce signals that cannot be easily processed.

In certain embodiments, the transducer comprises an Ion Sensitive Field Effect Transistor (ISFET). ISFET sensors are durable, low-power, inexpensive, and produce a current-based output signal, which can be readily amplified and processed. Additionally, ISFET sensors can be manufactured using CMOS methods, meaning they can be produced directly on the system on a chip. In some embodiments, the ISFET is fabricated to transduce the analyte ionic potential of protons in saliva to a time changing electrical current. In some embodiments, the transducer is manufactured by depositing a dielectric substrate over a molar band, on which an electrode pattern and thin film or nanotube conductor or semiconductor are deposited. In some embodiments, a reference electrode is also added. In some embodiments, the electrodes are made of conductive materials like gold, silver, or carbon, and the reference electrode is an Ag/AgCl paste, wire, or ink, and the channel is a graphene monolayer. In some embodiments, a semi-porous hydrogel is added as the gate insulator on top of the semiconductor with incorporated bioreceptors for specificity towards a certain analyte.

In some embodiments, the wearable intraoral sensor comprises more than one transducer. In certain embodiments, the wearable intraoral sensor comprises more than one ISFET sensor, wherein each sensor is configured to measure a different variable (e.g., pH, temperature, or an analyte). In some embodiments, each ISFET sensor is contained in a sensor housing comprising a semi-permeable membrane configured to allow detection of a certain variable by the ISFET sensor. In some embodiments, the ISFET sensor is installed on a supporting printed circuit board (PCB). In some embodiments, two or more additional ISFET sensors are added to the PCB to enable a multiplicity of molecules to be measured. Each ISFET uses a different membrane to enable the device to measure, for example, Na+, Ca2+, proteins, carbohydrates, fats, allergens, toxins, and other analytes described herein. These may be constructed from an array of conductive pads plated with gold, silver, platinum, etc., and may be commonly serviced with one or more reference electrodes also operating from one or more PCB pads. These pads would be connected to the signal processing circuitry using copper (or other) PCB traces which, can be routed on the top, bottom or through one or more layers of the PCB.

In some embodiments, the transducer may be encased in a protective housing such as a fabricated cube. In some embodiments, the top of the cube is made from a proton exchange membrane, which allows protons to diffuse through, and limits the diffusion of larger analytes. The housing protects the transducer from physical or chemical factors in the mouth. In some embodiments, the electrodes are patterned using methods including screen-printing, photolithography, evaporation, or physical vapor deposition (sputtering). In some embodiments, the graphene is fabricated using chemical vapor deposition on copper.

In some embodiments, the transducer is an ISFET with a conductive or semi-conductive channel material (graphene in some embodiments), to transduce the ionic potential (pH) surrounding the sensor to an electrical signal that can be transmitted.

In some embodiments, the wearable intraoral sensor measures pH in the oral cavity. In certain embodiments, the wearable intraoral sensor measures pH of saliva in the oral cavity. The pH of saliva can be influenced by various oral environmental factors, including, but not limited to, saliva, biofilm (tooth plaque), intrinsic and extrinsic oral fluids (including vapor), food, and breath.

In some embodiments, an ISFET sensor is modified to detect additional molecules in the oral cavity. In certain embodiments, the functional groups of the ISFET sensor are modified. Generally, the sensing membranes are modified by adding inorganic or organic chemical or biological receptors such as antibodies, aptomers, or small molecules depending on the analyte to be detected or measured. Additional analytes are described in Ana Carolina, *Recent Trends in Field-Effect Transistors-Based Immunosensors, Chemosensors* 2016, 4, 20, 21 Oct. 2016 (accessed here: http://www.mdpi.com:8080/2227-9040/4/4/20/pdf), which is herein incorporated by reference. Additional ISFET modifications are described at Torsi, *Organic field-effect transistors sensors: a tutorial review*, Chem Soc Rev., 21 Nov. 2013; 42(22):8612-28 (accessed here: https://www.ncbi.nlm.nih.gov/pubmed/24018860); and Lerner, *Detecting Lyme disease using antibody-functionalized single-walled carbon nanotube transistors*, Biosens Bioelectron. 15 Jul. 2013; 45:163-7 (accessed here https://www.ncbi.nlm.nih.gov/pubmed/23475141) which are incorporated by reference herein.

The wearable intraoral sensors of this disclosure collect and transmit reliable data. The sensors create reliable data with a two-prong approach. First, in static fluid settings, the output of the sensor consistently matches with a given pH value. This can be determined by adding various solutions with known pH values to the sensor, creating a calibration curve. The pH of unknown solutions can then be determined by measuring the sensor output, and comparing it later to the measured pH value of the solution. Solutions with similar chemical and physical consistencies to saliva should be tested.

The second prong is determining whether the sensor is able to measure pH accurately in the dynamic conditions of the mouth. The sensors of this disclosure account for the dynamic conditions of the mouth, including different salivary flow rates, turbidity, and viscosity, different contact from surrounding tissue like cheeks or tongue, as well as talking, yawning, chewing, and swallowing. In some embodiments, the reliability of the sensor's data is confirmed in a simulated mouth environment.

Through this two-prong approach, the sensors disclosed herein provide consistently reliable intraoral pH measurements.

In some embodiments, the transducers disclosed herein are designed to wrap around a molar band. In some embodiments, the molar band is metal. The molar band may but range in size from molar band size 22 mm to size 43+mm. The bands range from an upper diameter of around 8 mm and a lower diameter of around 9 mm, to an upper diameter of around 12 mm and a lower diameter of around 14 mm. In some embodiments, the electronics are printed on a flexible printed circuit board (PCB) which is adhered to the outer perimeter of the molar band, or printed onto the molar band.

The wearable intraoral sensors of this disclosure wirelessly transmit data. There are multiple main modes of data transmission. The modes of transmission are passive to the user, requiring little to no time commitment beyond initial installation of sensing device to receive data. The modes of transmission require little to no time commitment for charging or cleaning. The modes of transmission also do not require an intermediate receiver, which would force users to remember to wear the intermediate receiver, charge it, clean it, etc. In an embodiment with an active circuit, energy is provided by a chemical battery (nickel hydride batteries) to power the FET, amplify the signal from the FET, and transmit it to a smartphone or intermediate receiver via BLE (Bluetooth low energy), WLAN, Wi-Fi or ZigBee or another wireless communication technology described herein. In some embodiments, the transistor signal is sent through analog front end (AFE), to Balun, antenna, and BLE components. Some embodiments comprise similar electronic pathway with low pass filters to receive more stable readings.

In some embodiments, the wearable intraoral sensor wirelessly transmits via Bluetooth technology. In other embodiments, the wearable intraoral sensor wirelessly transmits via a wireless local area network (WLAN), Wi-Fi (wireless fidelity), ZigBee, near-field communication (NFC), ANT, Thread, Zigbee, WiMAX, WWAN, MANET, PAN, Wireless Hart, Z-Wave, MESH, UWB, IrDA, Cellular, Peer-To-Peer, and 802.11 variants. In still other embodiments, the wearable intraoral sensor wirelessly transmits via frequencies ranging from sub-sonic to ultraviolet. In further embodiments, the wearable oral sensor wirelessly transmits using modulation methods including, but not limited to, OOK, AM, FM, SSB, FSK, PSK, GFSK, and MSK. In still further embodiments, the wearable oral sensor wirelessly transmits using Near Field, Mid Field, or Far Field magnetic and or electric field radiation.

The tissue penetration profile of the signal may be determined by passing the signal through real animal tissue or simulated tissue with varying thickness.

In some embodiments, the molar band is configured to act as an antenna. This is accomplished through use of an impedance matching circuit from the SOC's radio transceiver to the metallic or semi-metallic structure of the molar band. Employing RF instrumentation such as a Vector Network Analyzer (VNA) the components comprising the impedance matching circuit, are adjusted in combination to cause resonance at the frequency of interest and thereby provide the optimal transfer of RF energy either flowing outwards towards the antenna or inwards toward the RF transceiver. As this adjustment process (tuning) must be performed in situ, it can be facilitated through use of external RF instrumentation which measures the radiated field strength from the device.

In some embodiments, the wearable intraoral sensor wirelessly transmits the signal comprising measurement data at intermittent intervals. In certain embodiments, the wearable intraoral sensor transmits the data signal once per minute. In some embodiments, the wearable intraoral sensor wirelessly transmits the data signal once every five minutes. In other embodiments, the wearable intraoral sensor wirelessly transmits the data signal once every ten minutes. In still other embodiments, the wearable intraoral sensor wirelessly transmits the data signal between once every minute and once every 30 minutes. In further embodiments, the wearable intraoral sensor wirelessly transmits the data signal immediately after the data signal is generated.

In further embodiments, the wearable intraoral sensor wirelessly transmits at different intervals depending on measurement time resolution against and life. These intervals range from immediate (once per millisecond) to long term (once per year) depending upon subject need(s) and the molecule(s) being measured. In still other embodiments, balancing measurement time resolution against battery life, sensor measurement data is stored in memory and then transmitted together as a single packet. In still other embodiments, balancing measurement time resolution against battery life, sensor measurements are stored in memory, and then transmitted as a single packet. In still yet other embodiments, balancing measurement time resolution against battery life, sensor data is conditionally wirelessly transmitted depending on when and/or how often measurement data deviate from predetermined values.

The wearable intraoral sensors of this disclosure comprise a power source. The described modes of data transmission work with a different powering mode. In embodiments with active circuits, power is delivered by an onboard battery to supply a source drain voltage and source gate voltage over the FET, amplify the signal, and transmit it. In previous research, a nickel hydride chemical coin battery was used, but only contained enough power for two weeks of data collection. Such power is insufficient.

In view of the limitations of this power source, new devices and methods to wirelessly recharge the battery in the mouth have been discovered. In some embodiments, a small plate capacitor is placed on the top of the tooth, which generates current as the user chews. By relying on Maxwell's equations, a current can be induced by changing the distance between the charged plates of a plate capacitor over time. Thus, in some embodiments, as the user chews, a small current is continuously generated and used to recharge the battery. In some embodiments, the battery may also be recharged by thermal gradients or chemical gradients within the mouth. In further embodiments, wireless inductive charging from an external source is used, so the user doesn't need to remove the sensor to recharge it. In still further embodiments, the sensor is removed and placed on a wireless inductive charging plate, similar to a wireless phone charger. However, this requires the user to remove the molar band sensor to charge it, potentially reducing subject compliance, and increasing user error.

In some embodiments, wireless communications and/or wireless charging can be accomplished by employing one or more windings of small diameter magnet wire around the perimeter of the molar band. For charging operations, the electric and/or magnetic field emanated from an external charging device would induce a corresponding electron flow in said coil which would be then rectified into DC current and supplied to the battery or storage capacitor. For communications operations, the same process is employed for receiving data excepting that this energy is directed towards the radio receiver. For transmitting data, the process is reversed wherein the radio transmitter induces an electric current in the winding, generating an electric and magnetic field that is sensed by an external device such as a receiving device described herein.

The wearable intraoral sensors of this disclosure can withstand damage from a variety of environmental factors, including damage via physical shear forces, damage via chemical corrosion, and formation of a biofilm or food layer over the sensing surface in the complex intraoral environment. In some embodiments, the sensor unit comprises a proton exchange membrane. In such embodiments, the transducer is exposed to salivary analytes only through a proton exchange membrane. The protons must diffuse across the membrane in order to reach the transducer. In some embodiments, the transducer is enclosed in a protective housing which protects the transducer from physical and other forces experienced in the mouth, prolonging sensing lifetime, and reducing noise.

Another significant hurdle is the formation of biofilm or food formation on the sensor. The wearable intraoral sensors disclosed herein overcome this hurdle in several ways. In some embodiments, the outer surface of the wearable intraoral sensor is made of an antifouling material that resists biofilm deposition, prolonging the lifetime of the device. In some embodiments, the sensor surface is chemically treated with antibiotics or hydrophobic compounds to prevent most materials from adhering. In some embodiments, the wearable intraoral sensor comprises an antimicrobial peptide coating. In some embodiments, the sensor is smooth with no pockets, jagged edges, gaps, or overhangs in which debris or bacteria can collect. In some embodiments, a physical antifouling surface (e.g., a geometric pattern) is engineered on the outside of the sensor, similar to sharkskin.

In some embodiments, the wearable intraoral sensor comprises a biocompatible epoxy which is ISO-10993-4,5,6,10, 11 approved. Such a coating can reduce irritation or inflammation of tissue surrounding the sensor in the oral cavity.

Methods of Installation

In some embodiments, the wearable intraoral sensors are designed to be installed by a dental provider. In embodiments where the wearable intraoral sensor comprises a molar band, a dental provider selects one molar on each side of the mandible to receive the band. In anticipation of orthodontic band placement, elastomeric separators are placed through the interproximal contacts of the mandibular (lower) molars to be banded, to create space for the bands to be seated. Next, the correct size band is selected for the subject. A correctly sized band will not be too loose but will have sufficient space for the placement of band cement. In some embodiments, a band is placed so the slot height of the band is in the middle of the tooth, with the indentation fitting into the mesio-buccal groove of the mandibular molar. Generally, an approximately equal amount of cusp height is visible from the buccal (cheekside) and lingual (tongue side) aspects of the molars that are banded. A band pusher or bite stick can be used to help seat the band. The tooth number and band size are etched onto the mesial (closer to the anterior midline) surface of the band, and should be noted, by the dentist, in the subject's records, for future reference. Once the band size is confirmed, the dentist chooses the appropriate wearable intraoral sensor for cementation. In some embodiments, the interior of the band is dried with a cotton roll or gauze and set aside. Then, in some embodiments, pumice is applied to the tooth by way of a prophy cup to remove the pellicle from the surface of the teeth. Next, resin modified glass ionomer cement, zinc oxide eugenol cement, zinc polycaboxylate cement, or resin cement, sometimes with fluoride release and flouride re-charging capability, is mixed on a glass slab with a mixing spatula. Cement is then placed, with the mixing spatula, covering the interior of the band. The band is seated using a band pusher or bite stick as needed. Excess cement is removed with a cotton roll or gauze before the cement sets. Once set, excess cement can be removed with a Mitchell trimmer or knotted floss passed through the interproximal contact points.

This disclosure provides methods for installing a wearable intraoral sensor comprising a molar band in an oral cavity of a subject. The method comprises selecting a molar in the oral cavity of the subject; sizing the selected molar for a molar band; creating space around the molar sufficient to fit the wearable intraoral sensor; applying adhesive to the molar band of the wearable intraoral sensor; installing the wearable intraoral sensor around the molar; and wirelessly syncing the wearable intraoral sensor to a receiving device.

In some embodiments, the method further comprises removing excess adhesive from the molar.

In some embodiments, the method further comprises syncing the wearable intraoral sensor to an application installed on the receiving device. In further embodiments, the method comprises adding identifying information of the subject to the application.

Methods for Measuring pH, Temperature, and Analytes in Subjects

The sensors of this disclosure can be worn by healthy subjects and subjects with various health conditions. Subjects who have many cavities and very poor oral health could greatly benefit from using this sensor. In some embodiments, subjects are informed throughout the day when their oral pH is approaching critical levels and taught to correct the imbalance in real time. In some embodiments, when a subject receives a notification of low oral pH, he or she will also receive recommendations for how to correct the imbalance in the mobile application (pH correcting mouthwash, pH correcting oral spray, brushing teeth, etc.). Furthermore, in some embodiments, dentists can track the data to identify trends in oral pH levels and better diagnose the source of the disease. If a subject's pH drops below 5.5 at night, caries could be occurring due to xerostomia or conditions that occur while sleeping. If the subject's pH drops after meals, the dentist could recommend different dietary habits. The sensor could also be used to track the effectiveness of treatments in between dental visits. The lifespan of permanent restorations, like crowns, root canals and implants will increase significantly if oral pH is maintained at a healthy level. In this way insurance companies will save on costs associated with re-treatment and dentists will be able to avoid misplaced blame for failing treatment. Individuals with mild and good oral health could also benefit from using this sensor in similar ways. They could be notified in real time whenever oral pH drops below the critical level and effectively prevent the onset of caries and receive recommendations in the mobile application on how to correct the oral pH via mouthwash, brushing teeth, or other corrective measures, before carious infections develop. This can save a great amount of pain and suffering from experiencing cavities, money spent on treating carious infections and time spent at dentists' offices. If caries do begin to occur, dentists can monitor the pH levels over time to better assess their origin and provide more personalized and effective treatments.

Another aspect of this disclosure is directed to a method for continually measuring pH or temperature or one or more analytes, or a combination thereof, in an oral cavity of a subject. The method comprises installing a wearable intraoral sensor of this disclosure in the oral cavity of the subject. This disclosure contemplates wearable intraoral sensors that can be inexpensively and quickly installed. Numerous existing dental devices, such as mouthguards, retainers, and dentures, require customization based on a subject's oral cavity. Such customizations require molding which requires a lot of time and expense.

In some embodiments, the sensor housing comprises a transducer, a data unit, a power source, and a proton exchange membrane. The sensor housing is connected to the dental installation with a seal so that fluid does not enter the sensor housing. In some embodiments, saliva directly contacts the membrane of the transducer.

In some embodiments, the wearable intraoral sensor is configured to continually measure pH in the oral cavity for at least one day. In other embodiments, the wearable intraoral sensor is configured to continually measure pH in the oral cavity for at least one week. In further embodiments, the wearable intraoral sensor is configured to continually measure pH in the oral cavity for at least one month. In still further embodiments, the wearable intraoral sensor is configured to continually measure pH in the oral cavity for a time ranging from one day to six months.

The method also comprises measuring pH or temperature or one or more analytes, or a combination thereof, in the oral cavity of the subject for at least one day, thereby generating measurement data. In some embodiments, the measurement data is pH measurement data, temperature measurement data, analyte measurement data, or a combination thereof.

The method also comprises wirelessly transmitting the measurement data from the wearable intraoral sensor at intermittent intervals. In certain embodiments, the measurement data is wirelessly transmitted once per minute. In some embodiments, the measurement data is wirelessly transmitted once every five minutes. In other embodiments, the measurement data is wirelessly transmitted once every ten minutes. In still other embodiments, the data measurement data is wirelessly transmitted between once every minute and once every 30 minutes. In further embodiments, the measurement data is wirelessly transmitted immediately after the data signal is generated. In certain embodiments, measured data is transmitted when requested by the receiving device at variable, non-defined intervals.

In some embodiments, the dental installation is a molar band sized to fit around a molar in the oral cavity of the subject. In some embodiments, the dental installation is a dental crown (also called a "dental cap") in the oral cavity of the subject. In other embodiments, the dental installation is a dental implant, bridge, dentures, orthodontic anchor, and/or any dental prosthesis in the oral cavity of the subject.

In some embodiments of the method, the transducer is an ion sensitive field effect transistor.

In some embodiments, the method further comprises wirelessly transmitting the measurement data from the molar band at intermittent intervals to a receiving device. In some embodiments, the receiving device is a smart device. In certain embodiments, the smart device is a smart phone, a smart watch, a tablet, smart home device (e.g., an Amazon Echo™ or other device using Amazon Alexa™, a Google Home™ device, or an Apple Home Pod™ or other device using Apple's Siri™) or a computer. In still further embodiments the smart device is an iPhone or Android phone. In some embodiments, the method further comprises configuring the receiving device or smart device to receive the measurement data. In certain embodiments, configuring a receiving device or smart device to receive the measurement data comprises installing an application on the receiving device or smart device.

In some embodiments, the method comprises wirelessly transmitting measurement data to Apple, Android, Nokia or other smartphones comprising Bluetooth, WiFi and/or Near Field communications capabilities. In some embodiments, the receiving device is a laptop, PC, or other smart device equipped with Bluetooth, WiFi, and/or Near Field communications capabilities. In some embodiments, the receiving device acts as a "relay station" and sends measurement data to the Internet, the "Cloud," or to another computer systems. In still yet another embodiment, the receiving device is an Apple, Google, or Amazon "Smart Home" device (e.g., a Siri-enabled, Google Home-enabled, or Alex-enabled device) which, in addition to functioning as a relay station, can interact with the subject wearing the wearable intraoral sensor.

In some embodiments, the receiving device is a custom product specifically designed for use with the wearable intraoral device. The custom device can provide for a variety of audio, visual, or haptic methods for interaction with the subject. These may include, but are not limited to, LEDs, speakers, vibrators, and text or graphic displays.

Existing devices and methods do not display to a subject data measured in the subject's oral cavity. In some embodiments, the application is configured to display measurement data on the display of the receiving device. In some embodiments, the application is configured to display measurement data in graphical form on the display of the receiving device. In further embodiments, the application is configured to display measurement data over time in graphical form on the display of the receiving device. In still further embodiments, the application is configured to display pH measurement data over time in graphical form with an indication of a critical pH value on the display of the receiving device.

In some embodiments, the method further comprises transmitting subject data from the receiving device or smart device to a medical office or dental office. In other embodiments, the method further comprises transmitting subject data from the receiving device or smart device to a research institution or a corporation. In still other embodiments, the method further comprises comprising syncing data between the wearable intraoral sensor and the receiving device or smart device.

In further embodiments, the method further comprises orienting the wearable intraoral sensor housing is oriented buccally to measure pH or temperature or one or more analytes, or a combination thereof, from saliva gathered in the cheek of a subject. In some embodiments, the method comprises orienting the transducer proton exchange membrane buccally.

Long-Term Intraoral Data Measurement Systems

Another aspect of this disclosure provides systems for continually monitoring pH in an oral cavity of a subject. Systems comprise a wearable intraoral sensor, as described herein, installed in an oral cavity of a subject. Systems also comprise a receiving device external to the oral cavity of the subject and configured to receive measurement data wirelessly transmitted from the wearable intraoral sensor.

In some embodiments, the receiving device is a mobile device. In certain embodiments, the smart device is a smart phone, a smart watch, a tablet, or a computer. In still further embodiments the smart device is an iPhone or Android phone. In some embodiments the receiving device comprises a display.

In some embodiments, the receiving device comprises a display. In certain embodiments, the receiving device is configured to display the measurement data, or a manipulation thereof, on a display. In still further embodiments, the receiving device is configured to display the measurement data, or a manipulation thereof, in graphical form on a display. In certain embodiments, the receiving device is configured to display the measurement data, or a manipulation thereof, in graphical form on a display and update the measurement data, or manipulation thereof, in real-time, as measurement data are generated.

In other embodiments, the systems further comprise an application installed on the receiving device for manipulating the measurement data. In some embodiments, the application comprises a user interface configured to interact with a user. In certain embodiments, the application is configured to display measurement data, or a manipulation thereof. In further embodiments, the application is configured to display measurement data, or a manipulation thereof, in graphical form. In still further embodiments, the application is configured to display an alert or play an audible alert or cause the receiving device to vibrate, or a combination thereof, when measurement data meet certain criteria. In some embodiments, the application is configured to determine whether measurement data meet criteria for a disorder or the potential development of a disorder. In particular embodiments, the application is configured to display an alert or play an audible alert or both when measurement data match threshold criteria. In some embodiments, the pH data is measured within a range of pH 2.0 to pH 10.0, and the threshold pH is set at pH 5.5. In certain embodiments, when pH is measured below pH 5.5 for specified periods of time, the application displays an alert or plays an audible alert or both. The specified periods of time can range in duration. For example, minimum duration can be set for a time ranging from two minutes to 120 minutes.

In other embodiments of the systems, devices and methods herein, macronutrient data is measured. In certain embodiments, the macronutrient data is consumed grams of protein, carbohydrates, fats, and/or calories. In certain embodiments, the application is configured to play an audible alert or display a message alerting the subject when specific dietary thresholds are met or approached (e.g., 2000 calories, 100 grams of fat). In further particular embodiments, allergen data is measured by presence of potential allergen-related molecules. In certain embodiments, the application is configured to play an audible alert and/or display a message alert when a potential allergen has been detected or has attained minimum concentration levels (e.g., concentration of peanut proteins increased from 10 ppm to 30 ppm).

In some embodiments, the criteria comprise criteria for diagnosing caries disease, HIV, viral and bacterial pathogens including herpes, hepatitis, HIV, HPV, influenza, polio, *E. coli, Myobacterium tuberculosis, Helicobacter pylori, Treponema pallidum, Candida albicans, Toxoplasma gondii*, and *Schistosoma mansoni*, cardiovascular disease (CVD), oral squamous cell carcinoma (OSCC), oral infection, hyperglycemia, hypertension, renal disease, stress, pain, periodontal disease, type 1 and type 2 diabetes, Lupus Erythematosis, oropharyngeal candidiasis (OPC), Scleroderma, Sjogren's syndrome, lymphoma, prostate cancer, breast cancer and tongue cancer.

In certain embodiments, the criteria are customized depending on variables specific to the subject. In some embodiments, the criteria comprise subject-specific risk factors.

In some embodiments, the receiving device is also configured to send measurement data to a receiving server. In certain embodiments, the receiving device is also configured to send subject identifying information to a receiving server.

In some embodiments, the system further comprises a receiving server configured to receive measurement data from the receiving device. In some embodiments, the receiving server is configured to determine whether measurement data indicates the development or potential development of a disorder in the subject. In further embodiments, the receiving server comprises criteria for determining whether measurement data indicates the development or potential development of a disorder in a subject. In still further embodiments, the receiving server is operably linked to one or more databases or one or more additional servers or a combination thereof for determining whether measurement data indicates the development or potential development of a disorder in the subject. In still other embodiments, the receiving server is configured to send a message to the receiving device. In some embodiments, the message comprises information related to the development or potential development of a disorder in the subject. In some embodiments, the message comprises instructions for the application to display an alert on the display of the receiving device or to play an audible alert or both.

In some embodiments, the criteria are criteria for diagnosing caries disease or the potential for development of caries disease.

In certain embodiments, the criteria are customized depending on variables specific to the subject. In some embodiments, the criteria comprise subject-specific risk factors.

In some embodiments of the systems, the wearable intraoral sensor is configured to transmit the measurement data from the wearable intraoral sensor at intermittent intervals. In certain embodiments, the measurement data is wirelessly transmitted once per minute. In some embodiments, the measurement data is wirelessly transmitted once every five minutes. In other embodiments, the measurement data is wirelessly transmitted once every ten minutes. In still other embodiments, the data measurement data is wirelessly transmitted between once every minute and once every 30 minutes. In further embodiments, the measurement data is wirelessly transmitted immediately after the data signal is generated.

Methods of Diagnosing Disorders

Another aspect of this disclosure provides methods of diagnosing a disorder in a subject, comprising installing a wearable intraoral sensor as described herein. The method comprises measuring or detecting or monitoring pH, temperature, one or more analytes, or a combination thereof, in an oral cavity of a subject for at least one day, thereby generating measurement data. The method comprises wirelessly transmitting the measurement data to a receiving device. In some embodiments, the wireless transmitting requires no human effort and is continual. In some embodiments, the method also comprises receiving the measurement data in the receiving device. The method also comprises comparing the measurement data to criteria for a disorder, wherein a disorder is diagnosed when the measurement data matches the criteria for a disorder. In certain embodiments, the criteria can be customized depending on variables specific to the subject. In some embodiments, the method does not require any action by the subject.

In some embodiments, the method comprises measuring or detecting or monitoring pH, temperature, one or more analytes, or a combination thereof, in an oral cavity of a subject for at least one week. In other embodiments, the method comprises measuring or detecting or monitoring pH, temperature, one or more analytes, or a combination thereof, in an oral cavity of a subject for at least one week. In further embodiments, the method comprises measuring or detecting or monitoring pH, temperature, one or more analytes, or a combination thereof, in an oral cavity of a subject for a defined time period. In still further embodiments, the method comprises measuring or detecting or monitoring pH, temperature, one or more analytes, or a combination thereof, in an oral cavity of a subject for a time period ranging from one day to six months.

In some embodiments, the disorder is caries disease. In other embodiments, the disorder is GERD. In still other embodiments, the disorder is heart disease. In some embodiments, the disorder is hypoglycemia, hyperglycemia, hormonal imbalance, HIV, a large number of viral and bacterial pathogens including herpes, hepatitis, HIV, HPV, influenza, polio, *E. coli, Myobacterium tuberculosis, Helicobacter pylori, Treponema pallidum, Candida albicans, Toxoplasma gondii*, and *Schistosoma mansoni*, cardiovascular disease (CVD), oral squamous cell carcinoma (OSCC), oral infection, hyperglycemia, hypertension, renal disease, stress, pain, periodontal disease, type 1 and type 2 diabetes, Lupus Erythematosis, oropharyngeal candidiasis (OPC), Scleroderma, Sjogren's syndrome, lymphoma, prostate cancer, breast cancer or tongue cancer.

The method also comprises wirelessly transmitting the measurement data from the wearable intraoral sensor at intermittent intervals. In certain embodiments, the measurement data is wirelessly transmitted once per minute. In some embodiments, the measurement data is wirelessly transmitted once every five minutes. In other embodiments, the measurement data is wirelessly transmitted once every ten minutes. In still other embodiments, the data measurement data is wirelessly transmitted between once every minute and once every 30 minutes. In further embodiments, the measurement data is wirelessly transmitted immediately after the data signal is generated.

In some embodiments, the method further comprises wirelessly transmitting the measurement data at intermittent intervals. In further embodiments, the method comprises wirelessly transmitting measurement data at intermittent intervals to a receiving device. In some embodiments, the receiving device is a smart device. In certain embodiments, the smart device is a smart phone, a smart watch, a tablet, or a computer. In still further embodiments the smart device is an iPhone or Android phone. In some embodiments, the method further comprises configuring the receiving device or smart device to receive the measurement data. In certain embodiments, configuring a receiving device or smart device to receive the measurement data comprises installing an application on the receiving device or smart device.

In some embodiments, the method further comprises identifying a time period that the pH measured in the oral cavity was below a threshold value on a plurality of days. In some embodiments, the method further comprises identifying patterns of pH measured falling below a threshold value.

In some embodiments, the method further comprises displaying measurement data on a display of the mobile device. In certain embodiments, the method comprises displaying measurement data in graphical form.

In further embodiments, the methods further comprise sending measurement data to a dental office or medical office. In other embodiments, the method further comprises sending subject identifying information to a dental office or medical office. In still further embodiments, the methods further comprise adding measurement data to a medical record of the subject. In yet further embodiments, the methods further comprises sending measurement data to a research institution or to a corporation. In additional embodiments, the method further comprises removing or masking subject identifying information.

Another aspect of this disclosure is directed to automated computer-implemented methods of sending a message comprising a suggested product, the method comprising, receiving at a server, measurement data measured in the oral cavity of a subject over a time period of at least one day, wherein the measurement data is sent from an application installed on a mobile device, identifying a disorder or the potential for a disorder to develop in the subject based on the measurement data, identifying a product for treating the identified disorder, preparing a message comprising information about the product, and sending the message to the mobile device.

Automated Methods

This disclosure also provides automated methods of warning a subject about the potential development of a disorder. The method comprises installing a wearable intraoral sensor of this disclosure in a subject's oral cavity. The method also comprises measuring pH or temperature or one or more analytes, or a combination thereof, in the subject's oral cavity for a time period of at least one day, thereby generating measurement data. The method also comprises wirelessly transmitting the measurement data to a receiving device. The method also comprises comparing the measurement data to criteria for a disorder. The method comprises displaying an alert message on a display of the receiving device when the measurement data matches the criteria for a disorder.

In some embodiments, the method further comprises receiving the measurement data in an application on the mobile device.

In some embodiments, pH is measured. In other embodiments, temperature is measured. In further embodiments, an analyte is measured.

In some embodiments, the time period is at least one week. In further embodiments, the time period is at least one month. In still further embodiments, the time period ranges from one day to six months.

In some embodiments, the disorder is caries disease. In other embodiments, the disorder is another disorder described in this disclosure.

In some embodiments, the criteria comprise measured pH data at or below 5.5. In certain embodiments, the criteria comprise measured pH data at or below 5.5 for a specified duration. In still further embodiments, the criteria comprise risk factors specific to the subject.

In certain embodiments, the measurement data is wirelessly transmitted once per minute. In some embodiments, the measurement data is wirelessly transmitted once every five minutes. In other embodiments, the measurement data is wirelessly transmitted once every ten minutes. In still other embodiments, the data measurement data is wirelessly transmitted between once every minute and once every 30 minutes. In further embodiments, the measurement data is wirelessly transmitted immediately after the data signal is generated.

In some embodiments, the method further comprises displaying a message on the display of the receiving device, wherein the message comprises suggested corrective action.

Intraoral Monitor

FIG. 1 depicts an embodiment of a sensor unit of a wearable intraoral sensor mounted on metal molar band 102. Source electrodes 104 and drain electrodes 106 are to the left and the right of the semiconductor 108. The gate voltage is set by reference electrode 110. The transducer is mounted on insulating material 112 on molar band 102 and is contained within sensor unit 114. Transducer enclosure 114 protects the semiconducting channel (e.g., graphene or doped silicon) from tissue contact, microorganisms, or other particles. Transducer enclosure 114 is sealed from the mouth via proton exchange membrane (PEM) 116, which allows protons to cross the membrane and affect the gate voltage of the transducer. Chemically reactive membrane 118 is placed above semiconductor 108 and is able to accept and donate hydrogen to establish pH equilibrium with the external environment. Electrolyte permeable membrane 120 contains reference electrode 110. An antifouling membrane (not shown) is placed above PEM 116 to prevent material deposition and biofilm growth on PEM 116.

Electrodes 104 and 106 are supplied voltages by a microcontroller, and the source drain current is sent through analog frequency filters into the analog input of the transmission unit (not shown), also contained in transducer enclosure 114.

FIG. 2 depicts a perspective view of a wearable intraoral sensor's sensor unit, showing molar band 202 and proton exchange membrane 204 on sensor unit 206. Proton exchange membrane 204 allows protons selectively diffuse to the sensing electronics inside transducer enclosure 206. Transducer enclosure 206 contains a transducer (not shown) which is mounted on insulating material 210 on molar band 202. Housing unit 208 is shown in phantom to illustrate how housing unit 208 couples to molar band 202 and encloses transducer enclosure 206.

FIG. 3 is a perspective view of wearable intraoral sensor 300 with transducer enclosure 302 coupled to molar band 304 and enclosed by housing unit 306. Proton exchange membrane 308 allows protons to enter transducer enclosure 302.

FIG. 4 shows another perspective view of wearable intraoral sensor 400 with enclosed electronics for power, transmission, and transducing. The transducer is enclosed within transducer enclosure 406 exposed to the saliva via proton exchange membrane 402. The electronics are enclosed within transducer enclosure 406. The transducer, wireless transmission unit, and power source are enclosed in transducer enclosure 406 which is on molar band 408. Housing unit 404 is coupled to molar band 408. In some embodiments, transducer enclosure 406 and housing unit 404 are not separate components but a unitary piece configured to couple to molar band 408 and seal the electronics inside. In some embodiments, transducer enclosure 406 and housing unit 404 are separate components. In some embodiments, there is minimal material on the molar band interproximally, and the sensing, power, and transmission elements are positioned to protrude lingually and buccally.

Figure 5:
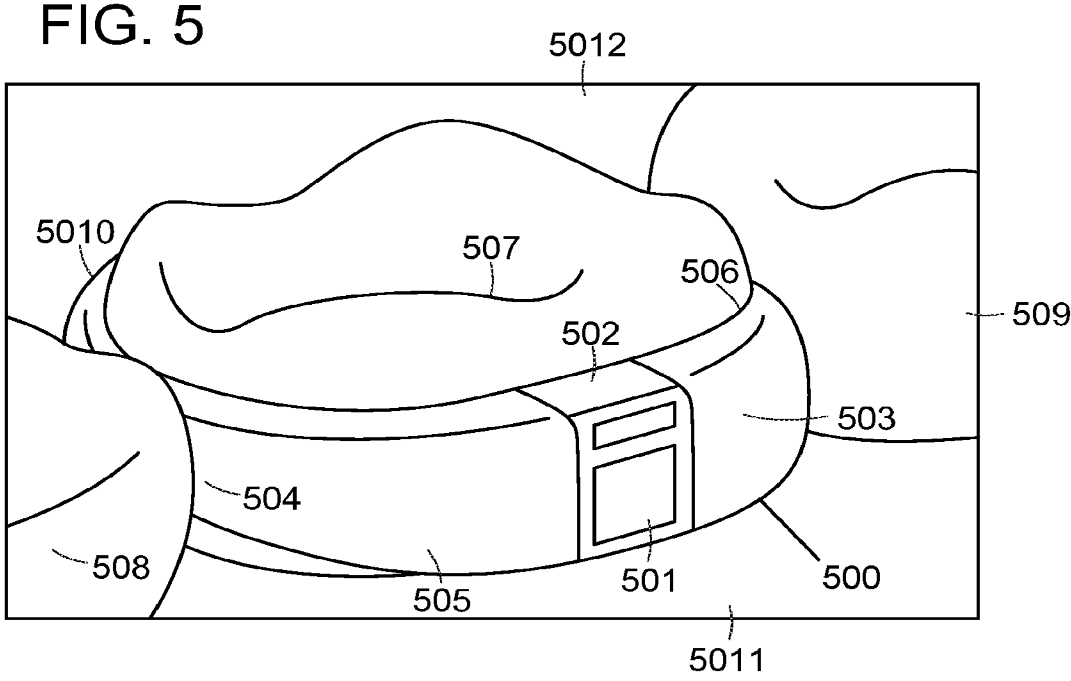
FIG. 5 is a perspective view of a wearable intraoral sensor installed in an oral cavity.

FIG. 5 is a perspective view of wearable intraoral sensor 500 installed in an oral cavity. Wearable intraoral sensor 500 is installed around molar 507 with surrounding teeth 508 and 509. Proton exchange membrane 501 is oriented buccally so it can be exposed to saliva pooling between molar 507, teeth 508, 509, gum 5011, and a cheek (not shown). Transducer enclosure 502 houses the transducer (not shown), and housing unit 505 houses the other electronics. In some embodiments, conditioning circuitry is inside wearable intraoral sensor 500 at or near location 503 to be near the transducer on the buccal side of molar band 506. In some embodiments, transmission, powering, and data storage electronics are oriented lingually towards tongue 5012 and located inside wearable intraoral sensor 500 at or near location 5010. Sensor housing 505 tapers at or near location 504 between interproximal teeth 508 and 509, in order to cause minimal noticeability in the mouth.

Figure 6:
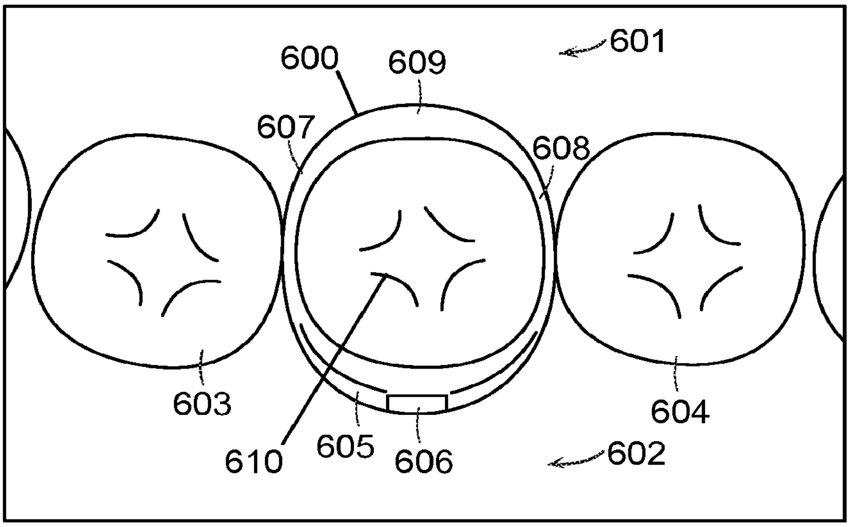
FIG. 6 a top view of wearable intraoral sensor 600 installed in an oral cavity.

FIG. 6 is a top view of wearable intraoral sensor 600 installed in an oral cavity. Wearable intraoral sensor 600 is installed around molar 6010 between surrounding teeth 603 and 604. The transducer enclosure 606 is oriented buccally so it can be exposed to saliva pooling between gum 602 and a cheek (not shown). Transducer enclosure 606 houses the transducer (not shown). Other electronics are enclosed within housing unit 607 houses. In some embodiments, conditioning circuitry within wearable intraoral sensor 600 is located at or near location 605 to be near the transducer on the buccal side of the molar band. In some embodiments, the transmission, powering, and data storage electronics within wearable intraoral sensor 600 are located at or near location 609 so they are oriented lingually towards tongue 601. Housing unit 607 tapers at location 608 between interproximal teeth 610 and 604, in order to cause minimal noticeability in the mouth.

Figure 7:
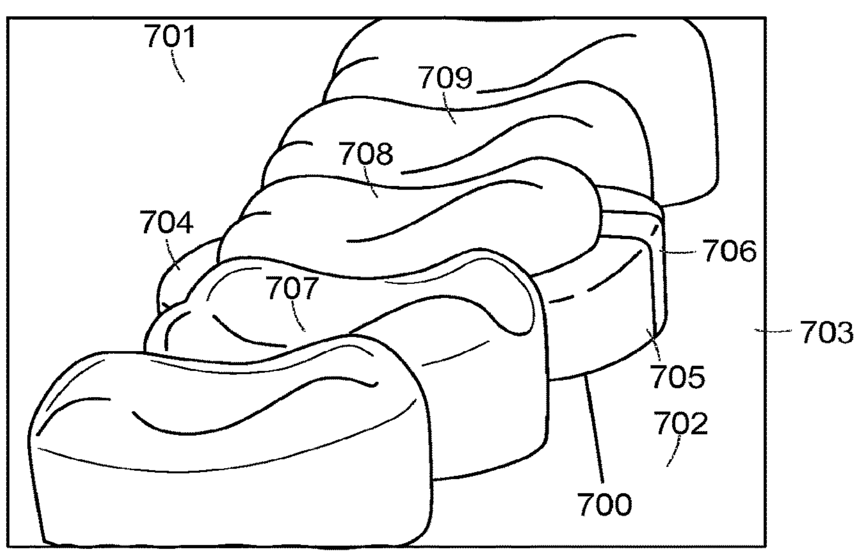
FIG. 7 is a perspective view of a wearable intraoral sensor installed in an oral cavity.

FIG. 7 is a perspective view of a wearable intraoral sensor installed in an oral cavity. Wearable intraoral sensor 700 is installed around molar 708 between surrounding teeth 707 and 709. Transducer enclosure 706 is oriented buccally so it can be exposed to saliva pooling between gum 702 and cheek 703. Transducer enclosure 706 houses the transducer (not shown). Housing 705 houses the other circuitry. In some embodiments, the conditioning circuitry is located near the transducer that is inside transducer housing 706 on the buccal side of wearable intraoral sensor. In some embodiments, the transmission, powering, and data storage electronics are oriented lingually towards the tongue 701 and located within wearable intraoral sensor 700 at or near location 704. Housing unit 705 tapers between interproximal teeth 707 and 709, in order to cause minimal noticeability in the mouth.

Figure 8:
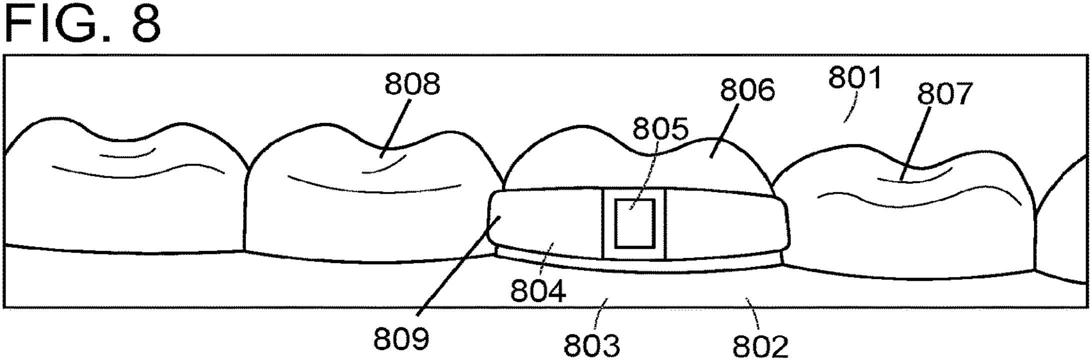
FIG. 8 is a side perspective view of wearable intraoral sensor 800 installed around a molar in an oral cavity.

FIG. 8 is a side perspective view of wearable intraoral sensor 800 installed around a molar in an oral cavity. Wearable intraoral sensor 800 is installed around molar 806 between surrounding teeth 807 and 808. Transducer enclosure 805 is oriented buccally so it can be exposed to saliva pooling between gum 803 and cheek 802. Transducer enclosure 805 houses the transducer. Housing unit 804 houses the other circuitry. In some embodiments, the conditioning circuitry is located near the transducer (not shown) that is inside transducer enclosure 805 on the buccal side of the molar band. In some embodiments, the transmission, powering, and data storage electronics are oriented lingually towards the tongue 801. Housing 804 tapers at location 809 between interproximal teeth 808 and 806 in order to cause minimal noticeability in the mouth.

Figure 9:
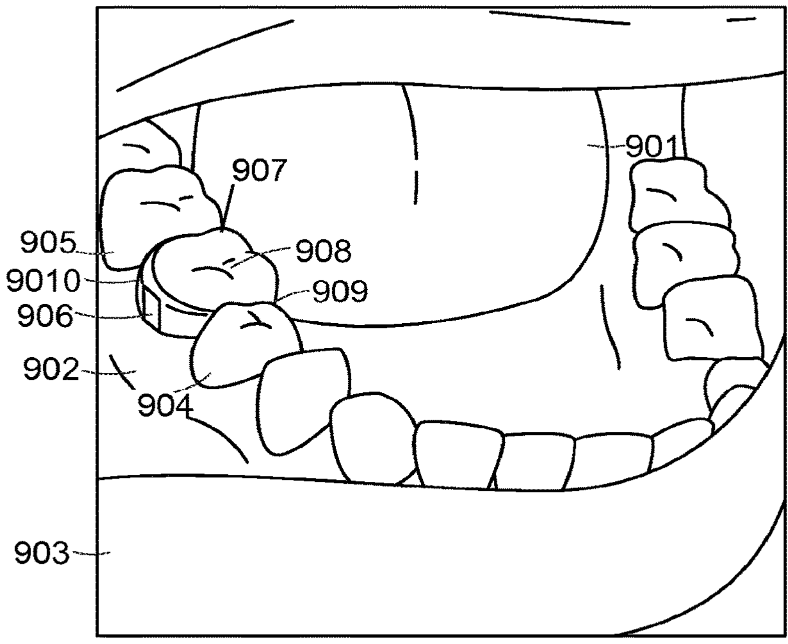
FIG. 9 depicts a perspective view of a wearable intraoral sensor installed in the oral cavity of a human.

FIG. 9 depicts a perspective view of a wearable intraoral sensor installed in the oral cavity of a human. Wearable intraoral sensor is installed around molar 908 between surrounding teeth 904 and 905. Transducer enclosure 906 is oriented buccally so it can be exposed to saliva pooling between gum 902 and cheek 903. Transducer enclosure 906 houses the transducer (not shown). Housing unit 9010 houses the other circuitry. In some embodiments, the conditioning circuitry is oriented near the transducer contained in transducer enclosure 906 on the buccal side of the wearable intraoral sensor. In some embodiments, the transmission, powering, and data storage electronics are located within wearable intraoral sensor at or near location 909 and oriented lingually towards the tongue 901. Housing unit 9010 tapers at location 907 between interproximal teeth 908 and 905, in order to cause minimal noticeability in the mouth.

Figure 9B:
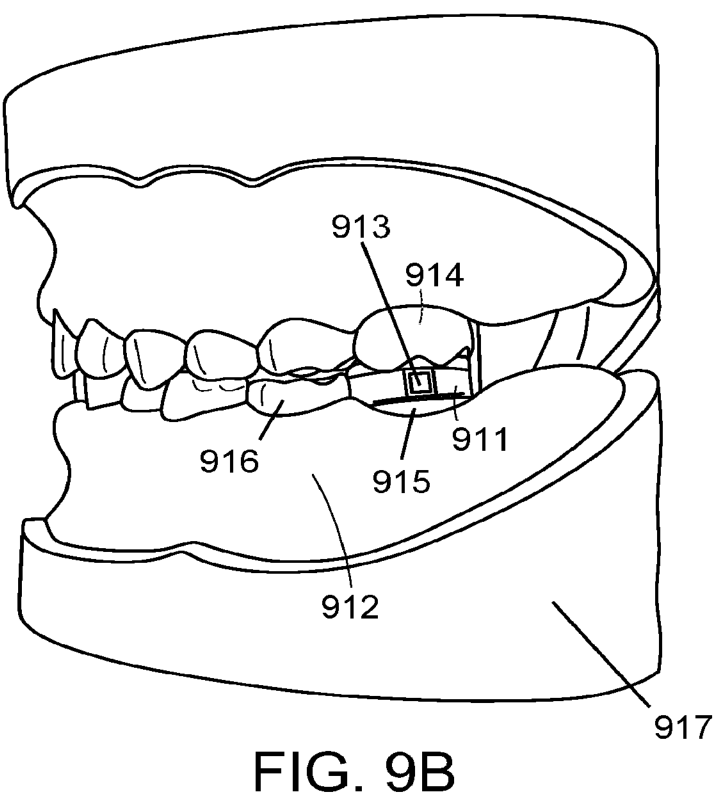
FIG. 9B depicts a side view of the wearable intraoral sensor in a typodont.

FIG. 9B depicts a side view of the wearable intraoral sensor in typodont 917, an anatomical model of a mouth, installed around molar 915. FIG. 9B shows adjacent tooth 916 and opposing tooth 914. The view shows how the wearable intraoral sensor does not protrude above the top of molar 915, and does not occlude the bite with opposing tooth 914. Transducer enclosure 913 is oriented buccally so it can be exposed to saliva pooling between gum 912 and cheek (not shown). Transducer enclosure 913 houses the transducer. Housing unit 911 houses the other circuitry. In some embodiments, the conditioning circuitry is oriented near the transducer contained with transducer enclosure 913 on the buccal side of the wearable intraoral sensor. In some embodiments, the transmission, powering, and data storage electronics are oriented lingually towards the tongue. Housing unit 911 tapers between interproximal tooth 916 and molar 915 in order to cause minimal noticeability in the mouth.

Figures 10A, 10B, 10C:
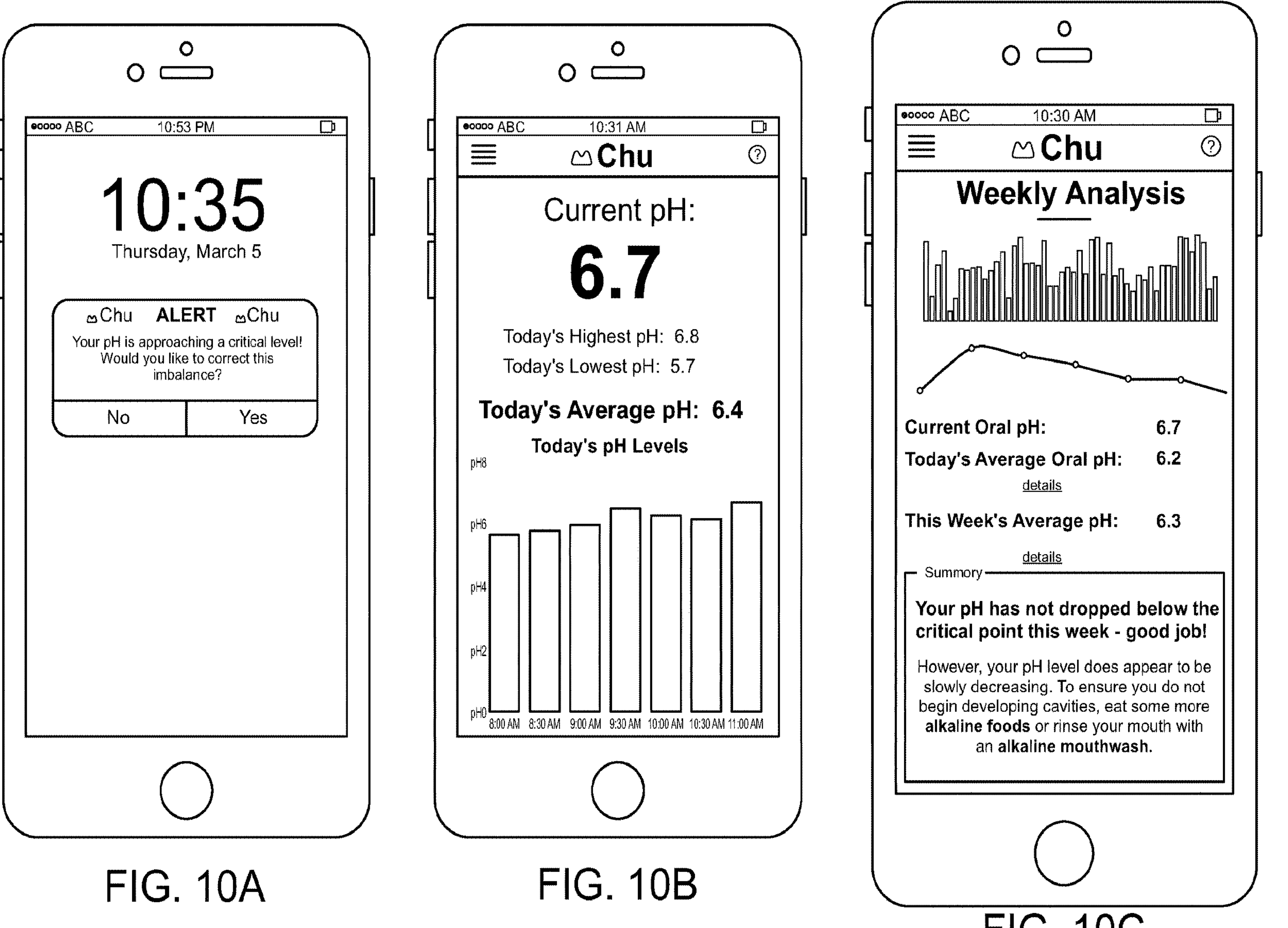
FIG. 10A shows an example of an alert displayed on a mobile device.
FIG. 10B shows a depiction of pH data displayed on a mobile device.
FIG. 10C depicts a display of data on a mobile device.

FIG. 10A shows an example of an alert displayed on a mobile device when pH measurement data meet a critical threshold. FIG. 10B shows a depiction of pH data displayed on a mobile device. FIG. 10C depicts a display of data showing the time changing electrical output of the wearable intraoral sensor, corresponding to changes measured in salivary pH.

Figure 11:
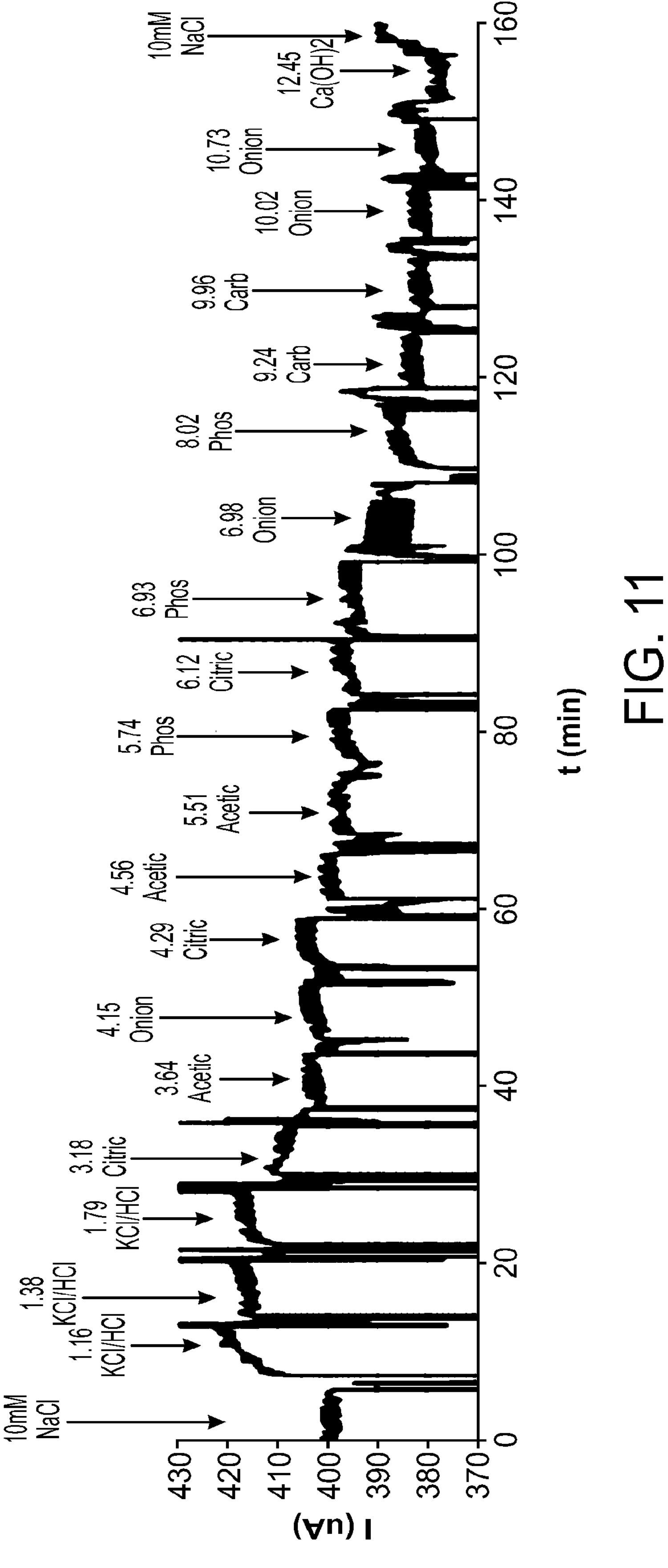
FIG. 11 is a graphical representation of the current through the ISFET channel as a function of time.

FIG. 11 is a graphical representation of the current through the ISFET channel (I) as a function of time (min). In this experiment, the ISFET is exposed to pH buffers made with standard international union of pure and applied chemistry (IUPAC) recipes. Initially the ISFET is exposed to a 10 mM NaCl solution. The solution is replaced with buffers of varying pH, starting with a pH of approximately 1 and ending with a pH of approximately 12.5. The solution is replaced roughly every 5 minutes, and the current output is continually measured using a data acquisition device.

Figure 12:
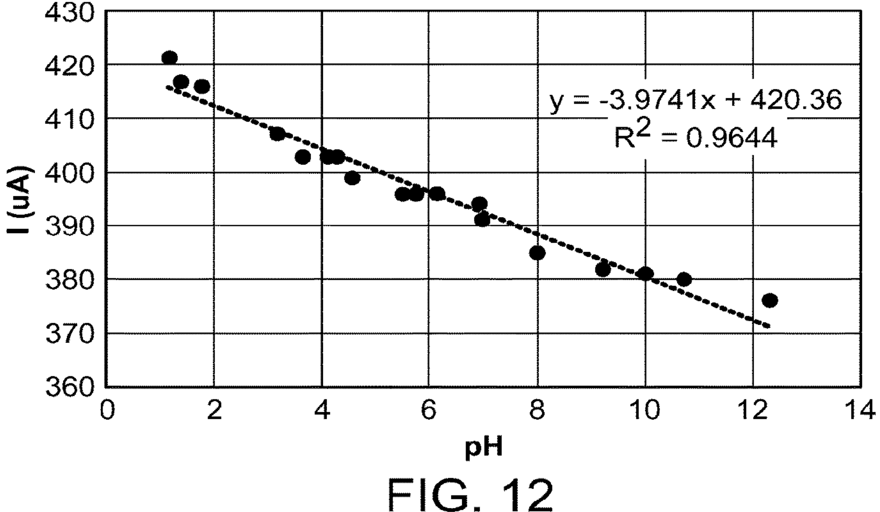
FIG. 12 is a graphical representation of the calibration curve observed from a pH ISFET.

FIG. 12 is a graphical representation of the calibration curve observed from a pH ISFET. The figure shows the current through the ISFET channel (I) as a function of the pH of the solution being measured. Once the mathematical equation of the relationship between pH and current is known, the pH of an unknown solution may be inferred based on the sensor's output. The equation for the relationship and the R^2 value, indicating linearity, is shown in the top right corner of the figure.

Figure 13:
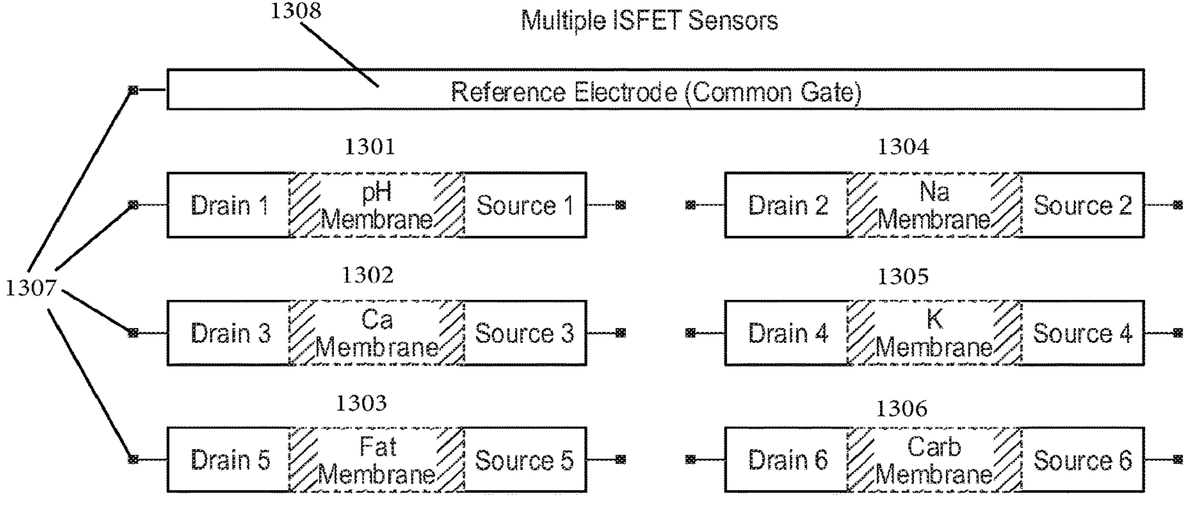
FIG. 13 is a depiction of an array of multiple ISFET sensors on a single wearable intraoral sensor.

FIG. 13 is a depiction of an array of multiple ISFET sensors sensitive to different analytes that can be included on a single wearable intraoral sensor to sense a multitude of different analytes. In some embodiments, multiple ISFET sensors are installed on the supporting printed circuit board (PCB) to measure a multiplicity of analytes or parameters. The six ISFETs shown in FIG. 13 each utilize a different membrane over the semiconducting channel that displays specificity towards specific analytes. As shown, ISFET 1301 has a membrane specific to protons, ISFET 1302 has a membrane specific to calcium ions, ISFET 1303 has a membrane specific toward fat molecules, ISFET 1304 has a membrane specific to sodium ions, ISFET 1305 has a membrane specific to potassium ions, and ISFET 1306 has a membrane specific toward carbohydrate molecules. Current and voltage is supplied to the ISFETs via the drain electrodes (Drain 1-6) via printed traces 1307 on the printed circuit board (Drains 2, 4, and 6 are not shown connected but would be connected). The drain electrodes may be constructed from an array of conductive pads plated with gold, silver, platinum, etc. Current passes through the semiconducting channels, and the output signal from the source is dependent on the specific analyte concentrations in the solution. The ISFETs gate voltage may be set by a common reference electrode 1308, supplied a voltage via trace 1307. The source and drain pads would be connected to the signal processing circuitry using copper (or other) PCB traces which can be routed on the top, bottom or through one or more layers of the PCB.

FIG. 14 depicts an exemplary block diagram for an embodiment of a wearable intraoral sensor. The wearable intraoral sensor comprises a molar band and various electronics which are mounted upon, or soldered to, a printed circuit board (PCB). The PCB material used can be of one or more layers of laminated fiberglass commonly referred to as "FR4".

The SOC (System on Chip) integrated circuit chip combines the functionality of a microcontroller and a radio transceiver into a single small package. Alternatively, the functionality of the SOC is implemented with a separate microcontroller and radio transceiver. The SOC sub-parts/modules/peripheral can include, but are not limited to, microcontroller, non-volatile memory, volatile memory, analog to digital converters (A/D), power conditioning circuitry and radio transceiver. The microcontroller can be, for example, an 8 Bit or other type, running at 64 MHz or other speed, and is based upon an ARM processor or other manufacturer. Non-volatile memory is used to store application software which controls the operation of the wearable oral sensor. This can be of the Flash memory type, or other, and can be, for example, of 192 Kilobytes (192 KB) in size, or other. Volatile memory is used to temporarily store measurement or other data. This can be of the RAM type, or other, and be of 24 Kilobytes (24 KB) or other. The wearable intraoral sensor is low power consumption, particularly whilst in "Sleep" or "Stand-By" mode. In one embodiment, the SOC requires only 0.3 microamps (0.3 uA) whilst in "Sleep" mode providing for an extended period between battery or super-capacitor charging cycles and/or a minimum of charging pulses from energy harvesting methods. The "front-end" or inputs to the SOC is the A/D module. This is comprised of one or more analog to digital converters which can operate individually or be multiplexed feeding data into the microprocessor (uC) for processing. These can operate at 200 Kilo Samples Per Second (200 KSBS) or other and resolve the analog inputs to 12 Bits or to 1 part of 4,096 parts, or other resolution as required. The power supply module functions to optimize current requirements drawn from an external battery and/or super-capacitor for maximum efficiency. This may include controlling a "switching" DC/DC using "Buck" methods when the battery/super capacitor voltage is higher than needed for SOC operation, or in "Boost" mode when it is lower than required. It may also disengage these Buck or Boost modes of DC/DC switching, when the input voltage is at nominal levels. The radio transceiver module functions as both a receiver and transmitter which is the interface between the SOC and the external RF components and antenna. For transmission, it encodes data from the SOC and modulates a radio carrier according to the signaling protocol required. For receiving, it demodulates the incoming radio carrier signal, decodes it into data and sends it to the SOC. This radio transceiver, depending upon the network specifications, may implement, but are not limited to Bluetooth, ZigBee, or WiFi protocols, and may operate over a variety of frequencies including but not limited to, 5 GHz, 2.45 GHz, 915 MHz, 433.920 MHz or other, and, employ a variety of modulation methods including, but not limited to OOK, AM, FM, SSB, FSK, PSK, GFSK, and MSK. The functionality of the "radio" transceiver can be expanded upon to include, but are not limited to Near Field, Mid Field, and Far Field electric or magnetic communications.

In an exemplary embodiment, the ISFET consists of source and drain electrodes connected by a semiconducting channel, a gate electrode separated from the channel via an electrolyte solution, and an analyte-specific membrane deposited over the gate. The drain current passing through the channel is a function of the intrinsic properties of the ISFET, the bias voltages applied to the three ISFET electrodes, and the ionic potential of the electrolyte solution. In a constant voltage constant current (CVCC) biasing circuit, the current flowing through the semiconducting channel is kept constant, as is the voltage across the source and drain. In this scenario, a change in pH may be measured by a change in output voltage in the circuit.

One or more operational amplifiers (OP-AMPs) integrated circuit chips (IC) function to transduce the microvolt and or microampere level signal changes across the ISFET drain and source channel which are dependent upon the molecule being sensed and the semiconductor (graphene, silicon, cheese, etc.,) employed. Providing a high input impedance, the OP-AMP functions a buffer between the ISFET and the input to the SOC's A/D module. One or more OP-AMPs may be employed for amplification and or to adjust the output voltage or current to the parameters acceptable of the A/D module.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:

1. A method for continually measuring analytes in an oral cavity of a subject, comprising:

installing a wearable intraoral sensor in the oral cavity of the subject, wherein the wearable intraoral sensor comprises a sensor module comprising a transducer, a data unit, a power source operably coupled to the data unit, and a proton exchange membrane, wherein the sensor module is configured to continually measure at least one analyte in the oral cavity for at least one day; and a housing unit configured to enclose at least the transducer of the sensor module within the housing unit, wherein the housing unit and the proton exchange membrane are fixed relative to a tooth, and wherein the proton exchange membrane is configured to allow protons to pass from an exterior of the housing unit into an interior of the housing unit;

continually measuring the at least one analyte in the oral cavity of the subject for at least one day, thereby generating analyte measurement data; and wirelessly transmitting the analyte measurement data from the wearable intraoral sensor at intervals.

2. The method of claim 1, wherein a portion of the wearable intraoral sensor is configured as an antenna operably connected to a wireless transmission unit.

3. The method of claim 1, further comprising orienting the proton exchange membrane buccally in the oral cavity, wherein the housing unit further comprises an impermeable molar-side wall, and a buccal-side wall disposed opposite the molar-side wall and including the proton exchange membrane.

4. The method of claim 1, further comprising wirelessly transmitting the data signal at intervals for at least one day, one week, one month, two months, three months, or six months.

5. The method of claim 1, continually measuring at least one analyte in the oral cavity of the subject for at least one week, one month, two months, three months, or six months.

6. The method of claim 1, wherein the transducer comprises an ISFET sensor.

7. The method of claim 1, further comprising configuring a mobile device to receive the analyte measurement data from the wearable intraoral sensor.

8. The method of claim 7, wherein configuring a mobile device to receive the analyte measurement data from the wearable intraoral sensor comprises installing an application on the mobile device.

9. The method of claim 8, further comprising transmitting subject data from the mobile device to a third party, wherein the subject data comprises the measurement data, subject identifying information, location information, device type, or a combination thereof.

10. The method of claim 9, wherein the third party is selected from the group consisting of a doctor, dentist, medical office, dental office, parent, relative, insurance agency, an insurance office and a research office.

11. The method of claim 7, further comprising syncing data from the wearable intraoral sensor and the mobile device.

12. The method of claim 1, wherein the housing unit comprises:

a molar-side wall; and a buccal-side wall, the buccal-side wall disposed opposite the molar-side wall;

wherein the molar-side wall is coextensive with a molar band, the molar-side wall configured to abut a molar in the oral cavity of the subject.

* * * * *